(12) United States Patent
Murakami et al.

(10) Patent No.: US 8,349,996 B2
(45) Date of Patent: Jan. 8, 2013

(54) COMPOUND, POLYMERIZABLE COMPOSITION, RESIN, AND USE OF THE COMPOSITION AND THE RESIN

(75) Inventors: Masakazu Murakami, Omuta (JP); Tomoyuki Ando, Omuta (JP); Seiichi Kobayashi, Omuta (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 13/055,280

(22) PCT Filed: Jul. 23, 2009

(86) PCT No.: PCT/JP2009/003480
§ 371 (c)(1),
(2), (4) Date: Jan. 21, 2011

(87) PCT Pub. No.: WO2010/013420
PCT Pub. Date: Feb. 4, 2010

(65) Prior Publication Data
US 2011/0130516 A1 Jun. 2, 2011

(30) Foreign Application Priority Data

Jul. 28, 2008 (JP) .................................. 2008-193215
Aug. 11, 2008 (JP) .................................. 2008-206844

(51) Int. Cl.
*C08G 75/00* (2006.01)
(52) U.S. Cl. .......................... 528/375; 528/373; 528/380
(58) Field of Classification Search .................. 528/375, 528/377, 380
See application file for complete search history.

(56) References Cited

U.S. PATENT DOCUMENTS

| 2005/0124783 A1 | 6/2005 | Morijiri et al. |
| 2005/0215757 A1 | 9/2005 | Kobayashi et al. |
| 2007/0191615 A1 | 8/2007 | Otsuji et al. |
| 2010/0063246 A1* | 3/2010 | Usugi et al. .................... 528/375 |
| 2010/0298519 A1* | 11/2010 | Nakamura et al. ................ 528/9 |

FOREIGN PATENT DOCUMENTS

| JP | 2003-327583 A | 11/2003 |
| JP | 2007-327060 A | 12/2007 |
| WO | WO 2005/095490 A1 | 10/2005 |
| WO | WO 2007/148432 A1 | 12/2007 |
| WO | WO 2008/102545 A1 | 8/2008 |

OTHER PUBLICATIONS

International Search Report (PCT/ISA/210) issued on Sep. 8, 2009, by Japanese Patent Office as the International Searching Authority for International Application No. PCT/JP2009/003480.

* cited by examiner

*Primary Examiner* — Shane Fang
(74) *Attorney, Agent, or Firm* — Buchanan Ingersoll & Rooney PC

(57) ABSTRACT

Disclosed is a compound represented by the following general formula (1),

[Chemical Formula 1]

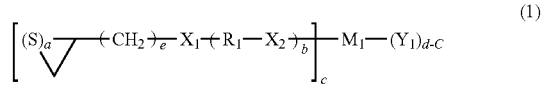

wherein, in the formula, $M_1$ represents Sb or Bi; $X_1$ and $X_2$ each independently represent a sulfur atom or an oxygen atom; $R_1$ represents a divalent organic group; $Y_1$ represents a monovalent inorganic or organic group; a represents a number of 1 or 2; b represents a number of 0 or an integer of not less than 1; c represents an integer of not less than 1 and not more than d; d represents a valence of $M_1$; when d–c is not less than 2, a plurality of $Y_1$s each independently represent a monovalent inorganic or organic group and may be bonded to each other to form an $M_1$-containing ring; and e represents a number of 0 or an integer of not less than 1.

16 Claims, No Drawings

US 8,349,996 B2

COMPOUND, POLYMERIZABLE COMPOSITION, RESIN, AND USE OF THE COMPOSITION AND THE RESIN

TECHNICAL FIELD

The present invention relates to a compound, a polymerizable composition, a resin, and the use of the composition and the resin.

BACKGROUND ART

In late years, a transparent organic polymer material has been used as a transparent material in place of an inorganic glass. When such a material is used, for example, for a resin for optical, there has been demanded the resin having required general properties such as transparency, thermal properties, mechanical properties and the like, while attaining a high refractive index.

A technique concerning such a resin has been disclosed in Patent Document 1. In the Document, a metal-containing thietane compound has been disclosed. Furthermore, a resin for optical having a high refractive index exceeding a refractive index (nd) of 1.7 has been disclosed.

Patent Document 1: International Publication Pamphlet No. 2005/095490

Patent Document 2: Japanese Patent Laid-open No. 2003-327583

DISCLOSURE OF THE INVENTION

However, there is room for improvement in view of enhancement of the refractive index of the transparent resin in the aforementioned technique.

The present invention is specified by matters described in below:

[1] a compound represented by the following general formula (1),

[Chemical Formula 1]

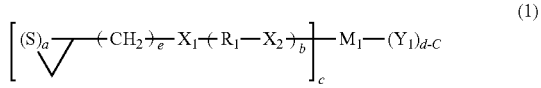

wherein, in the general formula (1), $M_1$ represents Sb or Bi; $X_1$ and $X_2$ each independently represent a sulfur atom or an oxygen atom; $R_1$ represents a divalent organic group; $Y_1$ represents a monovalent inorganic or organic group; a represents a number of 1 or 2; b represents a number of 0 or an integer of not less than 1; c represents an integer of not less than 1 and not more than d; d represents a valence of $M_1$; when d–c is not less than 2, a plurality of $Y_1$s each independently represent a monovalent inorganic or organic group and may be bonded to each other to form an $M_1$-containing ring; and e represents a number of 0 or an integer of not less than 1;

[2] the compound as set forth in [1], wherein $M_1$ is Sb;

[3] the compound as set forth in [1] or [2], wherein the general formula (1) is a compound represented by the following general formula (2),

[Chemical Formula 2]

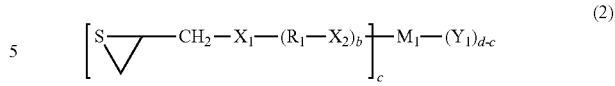

wherein, in the general formula (2), $M_1$ represents Sb or Bi; $X_1$ and $X_2$ each independently represent a sulfur atom or an oxygen atom; $R_1$ represents a divalent organic group; $Y_1$ represents a monovalent inorganic or organic group; b represents a number of 0 or an integer of not less than 1; c represents an integer of not less than 1 and not more than d; d represents a valence of $M_1$; and when d–c is not less than 2, a plurality of $Y_1$s each independently represent a monovalent inorganic or organic group and may be bonded to each other to form an $M_1$-containing ring;

[4] the compound as set forth in [3], wherein b is 0;

[5] the compound as set forth in [4], wherein $X_1$ is a sulfur atom;

[6] the compound as set forth in [5], wherein c and d are each 3;

[7] a polymerizable composition comprising the compound as set forth in any one of [1] to [6];

[8] the polymerizable composition as set forth in [7], comprising the compound as set forth in any one of [1] to [6], and at least one compound which is different from the compound as set forth in any one of [1] to [6] and selected from the group consisting of a thiol compound, an isocyanate compound, an episulfide compound, an epoxy compound, a non-metal thietane compound, a metal thietane compound, a (meth)acrylate ester compound, a vinyl compound and an oxetane compound;

[9] the polymerizable composition as set forth in [8], comprising a metal thietane compound represented by the following general formula (3),

[Chemical Formula 3]

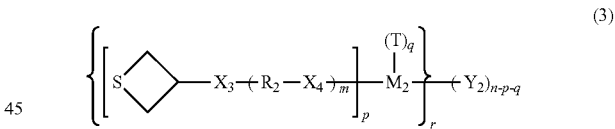

wherein, in the general formula (3), $M_2$ represents a metal atom; $X_3$ and $X_4$ each independently represent a sulfur atom or an oxygen atom; $R_2$ represents a divalent organic group; m represents a number of 0 or an integer of not less than 1; n represents a valence of $M_2$; p represents an integer of not less than 1 and not more than n; q represents a number of 0 or an integer of not less than 1 and not more than n–2; $Y_2$ represents a monovalent or divalent group; T represents an inorganic or organic group; r represents a number of 1 or 2;

when r is 1, $Y_2$ represents a monovalent inorganic or organic group, provided that r is 1 and n–p–q is not less than 2, a plurality of $Y_2$s each independently represent a monovalent inorganic or organic group, and provided that r is 1 and n–p–q is not less than 2, a plurality of $Y_2$s may be bonded to each other to form a ring containing a metal atom $M_2$;

when r is 2, and n–p–q is 1 or 2, $Y_2$ represents a divalent group, provided that r is 2 and n–p–q is 2, two $Y_2$s may form a ring along with two metal atoms $M_2$s, and provided that r is 2 and q is 2, a plurality of Ts each independently represent an inorganic or organic group;

[10] the polymerizable composition as set forth in [9], comprising a compound in which $M_2$ in the general formula (3) is Sb or Sn;

[11] the polymerizable composition as set forth in [9] or [10], comprising a compound in which $X_3$ in the general formula (3) is a sulfur atom;

[12] the polymerizable composition as set forth in any one of [9] to [11], comprising a compound represented by the following formula (4) as the compound represented by the general formula (3);

[Chemical Formula 4]

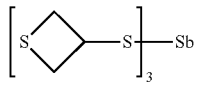

(4)

[13] the polymerizable composition as set forth in any one of [9] to [11], comprising a compound represented by the following formula (5) as the compound represented by the general formula (3);

[Chemical Formula 5]

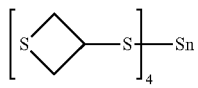

(5)

[14] the polymerizable composition as set forth in any one of [7] to [13], further comprising a bluing agent;

[15] a method for producing a resin, comprising a step of subjecting the polymerizable composition as set forth in any one of [7] to [14] to casting polymerization;

[16] a resin obtained by polymerizing the polymerizable composition as set forth in any one of [7] to [14];

[17] an optical component comprising the resin as set forth in [16];

[18] use of the polymerizable composition as set forth in any one of [7] to [14] as an optical component; and

[19] use of the resin obtained by polymerizing the polymerizable composition as set forth in any one of [7] to [14] as an optical component.

According to the present invention, there is provided a novel compound which obtains a transparent resin having a high refractive index.

BEST MODE FOR CARRYING OUT THE INVENTION

Hereinafter, the present invention will be described using concrete embodiments, but the present invention is not restricted to these embodiments. Furthermore, in the present invention, for respective components and groups, exemplified compounds may be used singly or in combination of a plurality thereof. Furthermore, an organic group may contain a hetero atom other than a carbon atom and a hydrogen atom in the group. Concrete examples of the hetero atom include an oxygen atom, a sulfur atom and a nitrogen atom.

The present invention relates to a compound having a cyclic structure containing S in the molecule, and having an Sb atom or a Bi atom.

Specifically, the present invention relates to a compound represented by the following general formula (1). This compound is suitable for use in optical components.

[Chemical Formula 6]

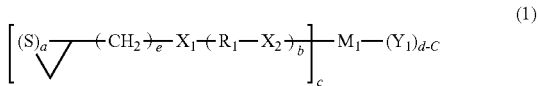

(1)

wherein, in the formula, $M_1$ represents Sb or Bi; $X_1$ and $X_2$ each independently represent a sulfur atom or an oxygen atom; $R_1$ represents a divalent organic group; $Y_1$ represents a monovalent inorganic or organic group;

a represents a number of 1 or 2;

b represents a number of 0 or an integer of not less than 1;

c represents an integer of not less than 1 and not more than d;

d represents a valence of $M_1$;

when d−c is not less than 2, a plurality of $Y_1$s each independently represent a monovalent inorganic or organic group and may be bonded to each other to form an $M_1$-containing ring; and e represents a number of 0 or an integer of not less than 1.

In the above formula (1), from the viewpoint of high refractive index and stability of a compound, e is preferably 1, and at this time, the above general formula (1) becomes the following general formula (6),

[Chemical Formula 7]

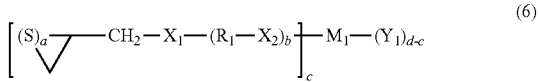

(6)

wherein, in the general formula (6), $X_1$, $X_2$, $R_1$, $Y_1$, $M_1$, a, b, c and d each represent the same as $X_1$, $X_2$, $R_1$, $Y_1$, $M_1$, a, b, c, d, respectively, in the above general formula (1).

By polymerizing the compound represented by the general formula (1), it is possible to obtain a transparent resin having a high refractive index.

In the above general formula, $X_1$ and $X_2$ each independently represent a sulfur atom or an oxygen atom. However, from the viewpoint of high refractive index of a resin obtained by polymerizing the compound represented by the general formula (1), it is preferable that $X_1$ and $X_2$ are each a sulfur atom. Also, it is preferable that b is 0, and c and d are the same.

Furthermore, in the above general formula (1), $R_1$ represents a divalent organic group.

Examples of such a divalent organic group include a chained or cyclic aliphatic group, an aromatic group and an aromatic-aliphatic group. From the viewpoint of high refractive index, preferably used are a chained aliphatic group having 1 to 20 carbon atoms, a cyclic aliphatic group having 3 to 20 carbon atoms, an aromatic group having 5 to 20 carbon atoms and an aromatic-aliphatic group having 6 to 20 carbon atoms.

In $R_1$, such a divalent organic group is more specifically a chained or cyclic aliphatic group, an aromatic group or an aromatic-aliphatic group. Preferable examples thereof include a substituted or unsubstituted chained or cyclic aliphatic group having 1 to 20 carbon atoms such as a methylene group, an ethylene group, a 1,2-dichloroethylene group, a trimethylene group, a tetramethylene group, a pentamethylene group, a cyclopentylene group, a hexamethylene group, a cyclohexylene group, a heptamethylene group, an octamethylene group, a nonamethylene group, a decamethylene group, an undecamethylene group, a dodecamethylene group, a tridecamethylene group, a tetradecamethylene group, a pentadecamethylene group and the like;

a substituted or unsubstituted aromatic group having 5 to 20 carbon atoms such as a phenylene group, a chlorophenylene group, a naphthylene group, an indenylene group, an anthracenylene group, a fluorenylene group and the like; and a substituted or unsubstituted aromatic-aliphatic group having 6 to 20 carbon atoms such as a —$C_6H_4$—$CH_2$— group, a —$CH_2$—$C_6H_4$—$CH_2$— group, a —$CH_2$—$C_6H_3$(Cl)—$CH_2$— group, a —$C_{10}H_6$—$CH_2$— group, a —$CH_2$—$C_{10}H_6$—$CH_2$— group, a —$CH_2CH_2$—$C_6H_4$—$CH_2CH_2$— group and the like.

$R_1$ is more preferably a substituted or unsubstituted chained or cyclic aliphatic group having 1 to 6 carbon atoms such as a methylene group, an ethylene group, a 1,2-dichloroethylene group, a trimethylene group, a cyclopentylene group, a cyclohexylene group and the like;

a substituted or unsubstituted aromatic group having 5 to 15 carbon atoms such as a phenylene group, a chlorophenylene group, a naphthylene group, an indenylene group, an anthracenylene group, a fluorenylene group and the like; or a substituted or unsubstituted aromatic-aliphatic group having 6 to 15 carbon atoms such as a —$C_6H_4$—$CH_2$— group, a —$CH_2$—$C_6H_4$—$CH_2$— group, a —$CH_2$—$C_6H_3$(Cl)—$CH_2$— group, a —$C_{10}H_6$—$CH_2$— group, a —$CH_2$—$C_{10}H_6$—$CH_2$— group, a —$CH_2CH_2$—$C_6H_4$—$CH_2CH_2$— group and the like.

Such a divalent organic group may contain a hetero atom other than a carbon atom and a hydrogen group in the group. Examples of the hetero atom include an oxygen atom and a sulfur atom. In consideration of the desired effect of the present invention, a sulfur atom is preferable.

In the above general formula (1), $M_1$ is Sb or Bi. Even when $M_1$ is any of Bi or Sb, the refractive index can be enhanced by the general formula (1).

Although Sb or Bi is trivalent or pentavalent, from the viewpoint of high refractive index, Sb or Bi is preferably trivalent. From the viewpoint of easy production and stability of the compound, $M_1$ is particularly preferably an Sb atom.

In the above general formula (1), when e is 1 and a is 1, the above general formula (1) becomes the following general formula (2),

[Chemical Formula 8]

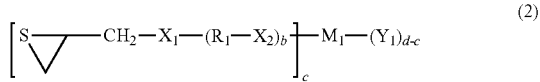

(2)

wherein, in the above general formula (2), $X_1$, $X_2$, $R_1$, $Y_1$, $M_1$, b, c and d each represent the same as $X_1$, $X_2$, $R_1$, $Y_1$, $M_1$, b, c, d, respectively, in the above general formula (1).

Furthermore, in the above general formula (2), in a group to be bonded to $M_1$ containing an episulfide group, namely, a group represented in [ ], b is further preferably 0. Further, b is 0, and $X_1$ is a sulfur atom. At this time, the above general formula (2) is represented by the following general formula (7),

[Chemical Formula 9]

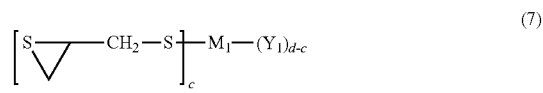

(7)

wherein, in the above general formula (7), $Y_1$, $M_1$, c and d each represent the same as $Y_1$, $M_1$, c and d in the above general formula (1).

In the above general formula (2), c and d are each preferably 3, while, in the above general formula (7), c and d are each further preferably 3. At this time, the above general formula (2) becomes a compound represented by the following formula (8),

[Chemical Formula 10]

(8)

wherein, in the above general formula (8), $M_1$ is the same as $M_1$ in the above general formula (1).

On the other hand, in the above general formula (1), when a is 2, the above general formula (1) becomes the following general formula (9),

[Chemical Formula 11]

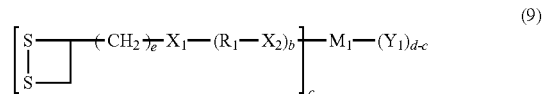

(9)

wherein, in the above general formula (9), $X_1$, $X_2$, $R_1$, $Y_1$, $M_1$, b, c, d, e each represent the same as $X_1$, $X_2$, $R_1$, $Y_1$, $M_1$, b, c, d, e, respectively, in the above general formula (1).

In the above general formula (9), in a group represented in [ ], it is further preferable that e is 1 and b is 0. Also, it is preferable that e is 1, b is 0 and $X_1$ is a sulfur atom. At this time, the above general formula (9) is represented by the following general formula (10),

[Chemical Formula 12]

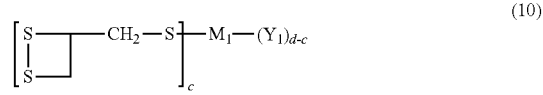

(10)

wherein, in the above general formula (10), $M_1$, $Y_1$, c and d each represent the same as $M_1$, $Y_1$, c and d in the above general formula (1).

In the above general formulae (9) and (10), c and d are each preferably 3. Further, in the above general formula (10), a valence of $M_1$: d is 3, and further when c is 1 or 2, $Y_1$ may be as follows,

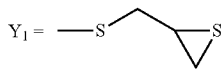
[Chemical Formula 13]

As described above, a compound in which a is 2 can be obtained by reacting sulfur with a compound in which a is 1 in the general formula (1).

Hereinafter, $Y_1$ will be described in detail.

$Y_1$ represents a monovalent inorganic or organic group.

$Y_1$ is not particularly limited, but examples thereof include a hydrogen atom, a halogen atom, a hydroxyl group, a thiol group, a substituted or unsubstituted alkyl group, a substituted or unsubstituted aryl group, a substituted or unsubstituted aralkyl group, a substituted or unsubstituted alkoxy group, a substituted or unsubstituted alkylthio group, a substituted or unsubstituted aryloxy group and a substituted or unsubstituted arylthio group.

Of these, the halogen atom, the substituted or unsubstituted alkyl group, the substituted or unsubstituted aryl group, the substituted or unsubstituted aralkyl group, the substituted or unsubstituted alkoxy (alkyloxy) group, the substituted or unsubstituted alkylthio group, the substituted or unsubstituted aryloxy group, and the substituted or unsubstituted arylthio group will be described below.

Concrete examples of the halogen atom include a fluorine atom, a chlorine atom, a bromine atom and an iodine atom.

Concrete examples of the substituted or unsubstituted alkyl group include a straight chained alkyl group having 1 to 10 carbon atoms in total such as a methyl group, an ethyl group, an n-propyl group, an n-butyl group, an n-pentyl group, an n-hexyl group and the like;

a branched alkyl group having 3 to 10 carbon atoms in total such as an isopropyl group, an isobutyl group, a sec-butyl group, an isopentyl group, a sec-pentyl group, a 1-methylpentyl group, a 2-methylpentyl group, a 3-methylpentyl group, a 4-methylpentyl group, a 1-ethylbutyl group, a 2-ethylbutyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 1-n-propylbutyl group, a 1-iso-propylbutyl group, a 1-iso-propyl-2-methylpropyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 1-n-propylpentyl group, a 2-n-propylpentyl group, a 1-iso-propylpentyl group, a 2-iso-propylpentyl group, a 1-n-butylbutyl group, a 1-iso-butylbutyl group, a 1-sec-butylbutyl group, a 1-tert-butylbutyl group, a 2-tert-butylbutyl group, a tert-butyl group, a tert-pentyl group, a 1,1-dimethylbutyl group, a 1,2-dimethylbutyl group, a 1,3-dimethylbutyl group, a 2,3-dimethylbutyl group, a 1-ethyl-2-methylpropyl group, a 1,1-dimethylpentyl group, a 1,2-dimethylpentyl group, a 1,3-dimethylpentyl group, a 1,4-dimethylpentyl group, a 2,2-dimethylpentyl group, a 2,3-dimethylpentyl group, a 2,4-dimethylpentyl group, a 3,3-dimethylpentyl group, a 3,4-dimethylpentyl group, a 1-ethyl-1-methylbutyl group, a 1-ethyl-2-methylbutyl group, a 1-ethyl-3-methylbutyl group, a 2-ethyl-1-methylbutyl group, a 2-ethyl-3-methylbutyl group, a 1,1-dimethylhexyl group, a 1,2-dimethylhexyl group, a 1,3-dimethylhexyl group, a 1,4-dimethylhexyl group, a 1,5-dimethylhexyl group, a 2,2-dimethylhexyl group, a 2,3-dimethylhexyl group, a 2,4-dimethylhexyl group, a 2,5-dimethylhexyl group, a 3,3-dimethylhexyl group, a 3,4-dimethylhexyl group, a 3,5-dimethylhexyl group, a 4,4-dimethylhexyl group, a 4,5-dimethylhexyl group, a 1-ethyl-2-methylpentyl group, a 1-ethyl-3-methylpentyl group, a 1-ethyl-4-methylpentyl group, a 2-ethyl-1-methylpentyl group, a 2-ethyl-2-methylpentyl group, a 2-ethyl-3-methylpentyl group, a 2-ethyl-4-methylpentyl group, a 3-ethyl-1-methylpentyl group, a 3-ethyl-2-methylpentyl group, a 3-ethyl-3-methylpentyl group, a 3-ethyl-4-methylpentyl group, a 1-n-propyl-1-methylbutyl group, a 1-n-propyl-2-methylbutyl group, a 1-n-propyl-3-methylbutyl group, a 1-iso-propyl-1-methylbutyl group, a 1-iso-propyl-2-methylbutyl group, a 1-iso-propyl-3-methylbutyl group, a 1,1-diethylbutyl group, a 1,2-diethylbutyl group, a 1,1,2-trimethylpropyl group, a 1,2,2-trimethylpropyl group, a 1,1,2-trimethylbutyl group, a 1,1,3-trimethylbutyl group, a 1,2,3-trimethylbutyl group, a 1,2,2-trimethylbutyl group, a 1,3,3-trimethylbutyl group, a 2,3,3-trimethylbutyl group, a 1,1,2-trimethylpentyl group, a 1,1,3-trimethylpentyl group, a 1,1,4-trimethylpentyl group, a 1,2,2-trimethylpentyl group, a 1,2,3-trimethylpentyl group, a 1,2,4-trimethylpentyl group, a 1,3,4-trimethylpentyl group, a 2,2,3-trimethylpentyl group, a 2,2,4-trimethylpentyl group, a 2,3,4-trimethylpentyl group, a 1,3,3-trimethylpentyl group, a 2,3,3-trimethylpentyl group, a 3,3,4-trimethylpentyl group, a 1,4,4-trimethylpentyl group, a 2,4,4-trimethylpentyl group, a 3,4,4-trimethylpentyl group, a 1-ethyl-1,2-dimethylbutyl group, a 1-ethyl-1,3-dimethylbutyl group, a 1-ethyl-2,3-dimethylbutyl group, a 2-ethyl-1,1-dimethylbutyl group, a 2-ethyl-1,2-dimethylbutyl group, a 2-ethyl-1,3-dimethylbutyl group, a 2-ethyl-2,3-dimethylbutyl group and the like; and a saturated cyclic alkyl group having 5 to 10 carbon atoms in total such as a cyclopentyl group, a cyclohexyl group, a methylcyclopentyl group, a methoxycyclopentyl group, a methoxycyclohexyl group, a methylcyclohexyl group, a 1,2-dimethylcyclohexyl group, a 1,3-dimethylcyclohexyl group, a 1,4-dimethylcyclohexyl group, an ethylcyclohexyl group and the like.

Concrete examples of the substituted or unsubstituted aryl group include an aromatic hydrocarbon group having not more than 20 carbon atoms in total such as a phenyl group, a naphthyl group, an anthranyl group, a cyclopentadienyl group and the like;

an alkyl-substituted aryl group having not more than 20 carbon atoms in total such as a 2-methylphenyl group, a 3-methylphenyl group, a 4-methylphenyl group, a 2-ethylphenyl group, a propylphenyl group, a butylphenyl group, a hexylphenyl group, a cyclohexylphenyl group, an octylphenyl group, a 2-methyl-1-naphthyl group, a 3-methyl-1-naphthyl group, a 4-methyl-1-naphthyl group, a 5-methyl-1-naphthyl group, a 6-methyl-1-naphthyl group, a 7-methyl-1-naphthyl group, a 8-methyl-1-naphthyl group, a 1-methyl-2-naphthyl group, a 3-methyl-2-naphthyl group, a 4-methyl-2-naphthyl group, a 5-methyl-2-naphthyl group, a 6-methyl-2-naphthyl group, a 7-methyl-2-naphthyl group, a 8-methyl-2-naphthyl group, a 2-ethyl-1-naphthyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, a 3,4,5-trimethylphenyl group and the like;

a monoalkoxyaryl group having not more than 20 carbon atoms in total wherein a substituted or unsubstituted alkyloxy group having not more than 10 carbon atoms is substituted, such as a 2-methoxyphenyl group, a 3-methoxyphenyl group, a 4-methoxyphenyl group, a 2-ethoxyphenyl group, a propoxyphenyl group, a butoxyphenyl group, a hexyloxyphenyl group, a cyclohexyloxyphenyl group, an octyloxyphenyl group, a 2-methoxy-1-naphthyl group, a 3-methoxy-1-naphthyl group, a 4-methoxy-1-naphthyl group, a 5-methoxy-1-naphthyl group, a 6-methoxy-1-naphthyl group, a 7-methoxy-1-naphthyl group, a 8-methoxy-1-naphthyl group, a 1-methoxy-2-naphthyl group, a 3-methoxy-2-naphthyl group, a 4-methoxy-2-naphthyl group, a 5-methoxy-2-naphthyl group, a 6-methoxy-2-naphthyl group, a 7-methoxy-2-naphthyl group, a 8-methoxy-2-naphthyl group, a 2-ethoxy-1-naphthyl group and the like;

a dialkoxyaryl group having not more than 20 carbon atoms in total wherein a substituted or unsubstituted alkyloxy group having not more than 10 carbon atoms is substituted, such as a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,6-dimethoxyphenyl group, a 4,5-dimethoxy-1-naphthyl group, a 4,7-dimethoxy-1-naphthyl group, a 4,8-dimethoxy-1-naphthyl group, a 5,8-dimethoxy-1-naphthyl group, a 5,8-dimethoxy-2-naphthyl group and the like;

a trialkoxyaryl group having not more than 20 carbon atoms in total wherein a substituted or unsubstituted alkyloxy group having not more than 10 carbon atoms is substituted, such as a 2,3,4-trimethoxyphenyl group, a 2,3,5-trimethoxyphenyl group, a 2,3,6-trimethoxyphenyl group, a 2,4,5-trimethoxyphenyl group, a 2,4,6-trimethoxyphenyl group, a 3,4,5-trimethoxyphenyl group and the like; and an aryl group having not more than 20 carbon atoms in total wherein a halogen atom is substituted, such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, a pentafluorophenyl group and the like.

Concrete examples of the substituted or unsubstituted aralkyl group include an aralkyl group having not more than 12 carbon atoms in total such as a benzyl group, a phenethyl group, a phenylpropyl group, a naphthylethyl group and the like. In addition thereto, there can be cited a methyl group, an ethyl group and a propyl group having an aryl group in a side chain specifically mentioned as examples of the substituted or unsubstituted aryl group beforehand.

Concrete examples of the substituted or unsubstituted alkyloxy group include a straight chained or branched alkoxy group having 1 to 10 carbon atoms in total such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, an iso-hexyloxy group, a 2-ethylhexyloxy group, a 3,5,5-trimethylhexyloxy group, an n-heptyloxy group, an n-octyloxy group, an n-nonyloxy group and the like;

a cycloalkoxy group having 5 to 10 carbon atoms in total such as a cyclopentyloxy group, a cyclohexyloxy group and the like;

an alkoxyalkoxy group having 2 to 10 carbon atoms in total such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, a tert-butoxyethoxy group, an n-pentyloxyethoxy group, an iso-pentyloxyethoxy group, an n-hexyloxyethoxy group, an iso-hexyloxyethoxy group, an n-heptyloxyethoxy group and the like; and an aralkyloxy group such as a benzyloxy group and the like.

Concrete examples of the substituted or unsubstituted alkylthio group include a straight chained or branched alkylthio group having 1 to 10 carbon atoms in total such as a methylthio group, an ethylthio group, an n-propylthio group, an iso-propylthio group, an n-butylthio group, an iso-butylthio group, a sec-butylthio group, a t-butylthio group, an n-pentylthio group, an iso-pentylthio group, an n-hexylthio group, an iso-hexylthio group, a 2-ethylhexylthio group, a 3,5,5-trimethylhexylthio group, an n-heptylthio group, an n-octylthio group, an n-nonylthio group and the like;

a cycloalkylthio group having 5 to 10 carbon atoms in total such as a cyclopentylthio group, a cyclohexylthio group and the like;

an alkoxyalkylthio group having 2 to 10 carbon atoms in total such as a methoxyethylthio group, an ethoxyethylthio group, an n-propoxyethylthio group, an iso-propoxyethylthio group, an n-butoxyethylthio group, an iso-butoxyethylthio group, a tert-butoxyethylthio group, an n-pentyloxyethylthio group, an iso-pentyloxyethylthio group, an n-hexyloxyethylthio group, an iso-hexyloxyethylthio group, an n-heptyloxyethylthio group and the like;

an aralkylthio group such as a benzylthio group and the like; and an alkylthioalkylthio group having 2 to 10 carbon atoms in total such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group, an n-pentylthioethylthio group, an iso-pentylthioethylthio group, an n-hexylthioethylthio group, an iso-hexylthioethylthio group, an n-heptylthioethylthio group and the like.

Concrete examples of the substituted or unsubstituted aryloxy group include an unsubstituted or alkyl-substituted aryloxy group having not more than 20 carbon atoms in total such as a phenyloxy group, a naphthyloxy group, an anthranyloxy group, a 2-methylphenyloxy group, a 3-methylphenyloxy group, a 4-methylphenyloxy group, a 2-ethylphenyloxy group, a propylphenyloxy group, a butylphenyloxy group, a hexylphenyloxy group, a cyclohexylphenyloxy group, an octylphenyloxy group, a 2-methyl-1-naphthyloxy group, a 3-methyl-1-naphthyloxy group, a 4-methyl-1-naphthyloxy group, a 5-methyl-1-naphthyloxy group, a 6-methyl-1-naphthyloxy group, a 7-methyl-1-naphthyloxy group, a 8-methyl-1-naphthyloxy group, a 1-methyl-2-naphthyloxy group, a 3-methyl-2-naphthyloxy group, a 4-methyl-2-naphthyloxy group, a 5-methyl-2-naphthyloxy group, a 6-methyl-2-naphthyloxy group, a 7-methyl-2-naphthyloxy group, a 8-methyl-2-naphthyloxy group, a 2-ethyl-1-naphthyloxy group, a 2,3-dimethylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, a 3,4,5-trimethylphenyloxy group and the like;

a monoalkoxyaryloxy group having not more than 20 carbon atoms in total wherein a substituted or unsubstituted alkyloxy group having not more than 10 carbon atoms is substituted, such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, a cyclohexyloxyphenyloxy group, an octyloxyphenyloxy group, a 2-methoxy-1-naphthyloxy group, a 3-methoxy-1- naphthyloxy group, a 4-methoxy-1-naphthyloxy group, a 5-methoxy-1-naphthyloxy group, a 6-methoxy-1-naphthyloxy group, a 7-methoxy-1-naphthyloxy group, a 8-methoxy-1-naphthyloxy group, a 1-methoxy-2-naphthyloxy group, a 3-methoxy-2-naphthyloxy group, a 4-methoxy-2-naphthyloxy group, a 5-methoxy-2-naphthyloxy group, a 6-methoxy-2-naphthyloxy group, a 7-methoxy-2-naphthyloxy group, a 8-methoxy-2-naphthyloxy group, a 2-ethoxy-1-naphthyloxy group and the like;

a dialkoxyaryloxy group having not more than 20 carbon atoms in total wherein a substituted or unsubstituted alkyloxy group having not more than 10 carbon atoms is substituted, such as a 2,3-dimethoxyphenyloxy group, a 2,4-dimethoxyphenyloxy group, a 2,5-dimethoxyphenyloxy group, a 2,6-dimethoxyphenyloxy group, a 3,4-dimethoxyphenyloxy group, a 3,5-dimethoxyphenyloxy group, a 3,6-dimethoxyphenyloxy group, a 4,5-dimethoxy-1-naphthyloxy group, a 4,7-dimethoxy-1-naphthyloxy group, a 4,8-dimethoxy-1-naphthyloxy group, a 5,8-dimethoxy-1-naphthyloxy group, a 5,8-dimethoxy-2-naphthyloxy group and the like;

a trialkoxyaryloxy group having not more than 20 carbon atoms in total wherein a substituted or unsubstituted alkyloxy group having not more than 10 carbon atoms is substituted, such as a 2,3,4-trimethoxyphenyloxy group, a 2,3,5-trimethoxyphenyloxy group, a 2,3,6-trimethoxyphenyloxy group, a 2,4,5-trimethoxyphenyloxy group, a 2,4,6-trimethoxyphenyloxy group, a 3,4,5-trimethoxyphenyloxy group and the like; and an aryloxy group having not more than 20 carbon atoms in total wherein a halogen atom is substituted, such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, a pentafluorophenyloxy group and the like.

Concrete examples of the substituted or unsubstituted arylthio group include an unsubstituted or alkyl-substituted arylthio group having not more than 20 carbon atoms in total such as a phenylthio group, a naphthylthio group, an anthranylthio group, a 2-methylphenylthio group, a 3-methylphenylthio group, a 4-methylphenylthio group, a 2-ethylphenylthio group, a propylphenylthio group, a butylphenylthio group, a hexylphenylthio group, a cyclohexylphenylthio group, an octylphenylthio group, a 2-methyl-1-naphthylthio group, a 3-methyl-1-naphthylthio group, a 4-methyl-1-naphthylthio group, a 5-methyl-1-naphthylthio group, a 6-methyl-1-naphthylthio group, a 7-methyl-1-naphthylthio group, a 8-methyl-1-naphthylthio group, a 1-methyl-2-naphthylthio group, a 3-methyl-2-naphthylthio group, a 4-methyl-2-naphthylthio group, a 5-methyl-2-naphthylthio group, a 6-methyl-2-naphthylthio group, a 7-methyl-2-naphthylthio group, a 8-methyl-2-naphthylthio group, a 2-ethyl-1-naphthylthio group, a 2,3-dimethylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, a 3,4,5-trimethylphenylthio group and the like;

a monoalkoxyarylthio group having not more than 20 carbon atoms in total wherein a substituted or unsubstituted alkyloxy group having not more than 10 carbon atoms is substituted, such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, a cyclohexyloxyphenylthio group, an octyloxyphenylthio group, a 2-methoxy-1-naphthylthio group, a 3-methoxy-1-naphthylthio group, a 4-methoxy-1-naphthylthio group, a 5-methoxy-1-naphthylthio group, a 6-methoxy-1-naphthylthio group, a 7-methoxy-1-naphthylthio group, a 8-methoxy-1-naphthylthio group, a 1-methoxy-2-naphthylthio group, a 3-methoxy-2-naphthylthio group, a 4-methoxy-2-naphthylthio group, a 5-methoxy-2-naphthylthio group, a 6-methoxy-2-naphthylthio group, a 7-methoxy-2-naphthylthio group, a 8-methoxy-2-naphthylthio group, a 2-ethoxy-1-naphthylthio group and the like;

a dialkoxyarylthio group having not more than 20 carbon atoms in total wherein a substituted or unsubstituted alkyloxy group having not more than 10 carbon atoms is substituted, such as a 2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, a 5,8-dimethoxy-2-naphthylthio group and the like;

a trialkoxyarylthio group having not more than 20 carbon atoms in total wherein a substituted or unsubstituted alkyloxy group having not more than 10 carbon atoms is substituted, such as a 2,3,4-trimethoxyphenylthio group, a 2,3,5-trimethoxyphenylthio group, a 2,3,6-trimethoxyphenylthio group, a 2,4,5-trimethoxyphenylthio group, a 2,4,6-trimethoxyphenylthio group, a 3,4,5-trimethoxyphenylthio group and the like; and an arylthio group having not more than 20 carbon atoms in total wherein a halogen atom is substituted, such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, a pentafluorophenylthio group and the like. $Y_1$ is not restricted thereto.

Preferable examples of $Y_1$ are as follows.

As a preferable example, there can be cited a hydrogen atom.

Furthermore, examples of the halogen atom among preferable examples of $Y_1$ include a chlorine atom, a bromine atom and an iodine atom.

Preferable examples of the substituted or unsubstituted alkyl group include a straight chained alkyl group having 1 to 6 carbon atoms in total such as a methyl group, an ethyl group, an n-propyl group, an n-butyl group, an n-pentyl group, an n-hexyl group and the like;

a branched alkyl group having 3 to 6 carbon atoms in total such as an isopropyl group, an isobutyl group, a sec-butyl group, an isopentyl group, a sec-pentyl group, a 1-methylpentyl group, a 2-methylpentyl group, a 3-methylpentyl group, a 4-methylpentyl group, a 1-ethylbutyl group, a 2-ethylbutyl group, a tert-butyl group, a tert-pentyl group, a 1,1-dimethylbutyl group, a 1,2-dimethylbutyl group, a 1,3-dimethylbutyl group, a 2,3-dimethylbutyl group and the like; and a saturated cyclic alkyl group having 5 or 6 carbon atoms in total such as a cyclopentyl group, a cyclohexyl group and the like.

Examples of the substituted or unsubstituted aryl group include an aromatic hydrocarbon group having not more than 12 carbon atoms in total such as a phenyl group, a naphthyl group, a cyclopentadienyl group and the like;

an alkyl-substituted aryl group having not more than 12 carbon atoms in total such as a 2-methylphenyl group, a 3-methylphenyl group, a 4-methylphenyl group, a 2-ethylphenyl group, a propylphenyl group, a butylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, a 3,4,5-trimethylphenyl group and the like;

a monoalkoxyaryl group having not more than 12 carbon atoms in total wherein a substituted or unsubstituted alkyloxy group having not more than 6 carbon atoms is substituted, such as a 2-methoxyphenyl group, a 3-methoxyphenyl group, a 4-methoxyphenyl group, a 2-ethoxyphenyl group, a propoxyphenyl group, a butoxyphenyl group and the like;

a dialkoxyaryl group having not more than 12 carbon atoms in total wherein a substituted or unsubstituted alkyloxy group having not more than 6 carbon atoms is substituted, such as a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,6-dimethoxyphenyl group and the like; and an aryl group having not more than 12 carbon atoms in total wherein a halogen atom is substituted, such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, a pentafluorophenyl group and the like.

Examples of the substituted or unsubstituted aralkyl group include an aralkyl group having not more than 12 carbon atoms in total such as a benzyl group, a phenethyl group, a phenylpropyl group and the like.

Examples of the substituted or unsubstituted alkyloxy group include a straight chained or branched alkoxy group having 1 to 6 carbon atoms in total such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, an iso-hexyloxy group and the like;

a cycloalkoxy group having 5 or 6 carbon atoms in total such as a cyclopentyloxy group, a cyclohexyloxy group and the like; and an alkoxyalkoxy group having 2 to 6 carbon atoms in total such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, a tert-butoxyethoxy group and the like.

Examples of the substituted or unsubstituted alkylthio group include a straight chained or branched alkylthio group having 1 to 6 carbon atoms in total such as a methylthio group, an ethylthio group, an n-propylthio group, an iso-propylthio group, an n-butylthio group, an iso-butylthio group, a sec-butylthio group, a t-butylthio group, an n-pentylthio group, an iso-pentylthio group, an n-hexylthio group, an iso-hexylthio group and the like;

a cycloalkylthio group having 5 or 6 carbon atoms in total such as a cyclopentylthio group, a cyclohexylthio group and the like;

an alkoxyalkylthio group having 2 to 6 carbon atoms in total such as a methoxyethylthio group, an ethoxyethylthio group, an n-propoxyethylthio group, an iso-propoxyethylthio group, an n-butoxyethylthio group, an iso-butoxyethylthio group, a tert-butoxyethylthio group and the like; and an alkylthioalkylthio group having 2 to 6 carbon atoms in total such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group and the like.

Examples of the substituted or unsubstituted aryloxy group include an unsubstituted or alkyl-substituted aryloxy group having not more than 12 carbon atoms in total such as a phenyloxy group, a naphthyloxy group, a 2-methylphenyloxy group, a 3-methylphenyloxy group, a 4-methylphenyloxy group, a 2-ethylphenyloxy group, a propylphenyloxy group, a butylphenyloxy group, a hexylphenyloxy group, a cyclohexylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, a 3,4,5-trimethylphenyloxy group and the like;

a monoalkoxyaryloxy group having not more than 12 carbon atoms in total wherein a substituted or unsubstituted alkyloxy group having not more than 6 carbon atoms is substituted, such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, a cyclohexyloxyphenyloxy group and the like;

a dialkoxyaryloxy group having not more than 12 carbon atoms in total wherein a substituted or unsubstituted alkyloxy group having not more than 6 carbon atoms is substituted, such as a 2,3-dimethoxyphenyloxy group, a 2,4-dimethoxyphenyloxy group, a 2,5-dimethoxyphenyloxy group, a 2,6-dimethoxyphenyloxy group, a 3,4-dimethoxyphenyloxy group, a 3,5-dimethoxyphenyloxy group, a 3,6-dimethoxyphenyloxy group and the like; and an aryloxy group having not more than 12 carbon atoms in total wherein a halogen atom is substituted, such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, a pentafluorophenyloxy group and the like.

Examples of the substituted or unsubstituted arylthio group include an unsubstituted or alkyl-substituted arylthio group having not more than 12 carbon atoms in total such as a phenylthio group, a naphthylthio group, a 2-methylphenylthio group, a 3-methylphenylthio group, a 4-methylphenylthio group, a 2-ethylphenylthio group, a propylphenylthio group, a butylphenylthio group, a hexylphenylthio group, a cyclohexylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, a 3,4,5-trimethylphenylthio group and the like;

a monoalkoxyarylthio group having not more than 12 carbon atoms in total wherein a substituted or unsubstituted alkyloxy group having not more than 6 carbon atoms is substituted, such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, a cyclohexyloxyphenylthio group and the like;

a dialkoxyarylthio group having not more than 12 carbon atoms in total wherein a substituted or unsubstituted alkyloxy group having not more than 6 carbon atoms is substituted, such as a 2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, a 5,8-dimethoxy-2-naphthylthio group and the like; and an arylthio group having not more than 12 carbon atoms in total wherein a halogen atom is substituted, such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, a pentafluorophenylthio group and the like.

More preferable examples of $Y_1$ are as follows.

A more preferable example of $Y_1$ includes a hydrogen atom. More preferable examples of the halogen atom include a chlorine atom and a bromine atom.

More preferable examples of the substituted or unsubstituted alkyl group include a straight chained or branched alkyl group having 1 to 3 carbon atoms in total such as a methyl group, an ethyl group, an iso-propyl group and the like.

More preferable examples of the substituted or unsubstituted aryl group include an aromatic hydrocarbon group having not more than 12 carbon atoms in total such as a phenyl group, a naphthyl group, a cyclopentadienyl group and the like;

an alkyl-substituted aryl group having not more than 9 carbon atoms in total such as a 2-methylphenyl group, a 3-methylphenyl group, a 4-methylphenyl group, a 2-ethylphenyl group, a propylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group and the like;

a monoalkoxyaryl group having not more than 9 carbon atoms in total wherein a substituted or unsubstituted alkyloxy group having not more than 3 carbon atoms is substituted, such as a 2-methoxyphenyl group, a 3-methoxyphenyl group, a 4-methoxyphenyl group, a 2-ethoxyphenyl group, a propoxyphenyl group and the like; and an aryl group having not more than 12 carbon atoms in total wherein a halogen atom is substituted, such as a chlorophenyl group, a dichlorophenyl group, a trichlorophenyl group, a bromophenyl group, a dibromophenyl group, a chloronaphthyl group, a bromonaphthyl group and the like.

More preferable examples of the substituted or unsubstituted aralkyl group include an aralkyl group having not more than 9 carbon atoms in total such as a benzyl group, a phenethyl group, a phenylpropyl group and the like.

More preferable examples of the substituted or unsubstituted alkyloxy group include a straight chained or branched alkoxy group having 1 to 3 carbon atoms in total such as a methoxy group, an ethoxy group, an iso-propoxy group and the like; and a cycloalkoxy group having 5 or 6 carbon atoms in total such as a cyclopentyloxy group, a cyclohexyloxy group and the like.

More preferable examples of the substituted or unsubstituted alkylthio group include a straight chained or branched alkylthio group having 1 to 3 carbon atoms in total such as a methylthio group, an ethylthio group, an n-propylthio group, an i-propylthio group and the like;

a cycloalkylthio group having 5 or 6 carbon atoms in total such as a cyclopentylthio group, a cyclohexylthio group and the like; and an alkylthioalkylthio group having 2 to 6 carbon atoms in total such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group and the like.

More preferable examples of the substituted or unsubstituted aryloxy group include an unsubstituted or alkyl-substituted aryloxy group having not more than 9 carbon atoms in total such as a phenyloxy group, a naphthyloxy group, a 2-methylphenyloxy group, a 3-methylphenyloxy group, a 4-methylphenyloxy group, a 2-ethylphenyloxy group, a propylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group and the like;

a monoalkoxyaryloxy group having not more than 9 carbon atoms in total wherein a substituted or unsubstituted alkyloxy group having not more than 3 carbon atoms is substituted, such as a 2-methoxyphenyloxy group, a 3-methoxyphenyloxy group, a 4-methoxyphenyloxy group, a 2-ethoxyphenyloxy group, a propoxyphenyloxy group and the like; and an aryloxy group having not more than 12 carbon atoms in total wherein a halogen atom is substituted, such as a chlorophenyloxy group, a dichlorophenyloxy group, a trichlorophenyloxy group, a bromophenyloxy group, a dibromophenyloxy group, a chloronaphthyloxy group, a bromonaphthyloxy group and the like.

More preferable examples of the substituted or unsubstituted arylthio group include an unsubstituted or alkyl-substituted arylthio group having not more than 9 carbon atoms in total such as a phenylthio group, a 2-methylphenylthio group, a 3-methylphenylthio group, a 4-methylphenylthio group, a 2-ethylphenylthio group, a propylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group and the like;

a monoalkoxyarylthio group having not more than 9 carbon atoms in total wherein a substituted or unsubstituted alkyloxy group having not more than 3 carbon atoms is substituted, such as a 2-methoxyphenylthio group, a 3-methoxyphenylthio group, a 4-methoxyphenylthio group, a 2-ethoxyphenylthio group, a propoxyphenylthio group and the like; and an arylthio group having not more than 12 carbon atoms in total wherein a halogen atom is substituted, such as a chlorophenylthio group, a dichlorophenylthio group, a trichlorophenylthio group, a bromophenylthio group, a dibromophenylthio group, a chloronaphthylthio group, a bromonaphthylthio group and the like.

When $Y_1$s do not form a ring, further concrete examples of $Y_1$ include an alkyl group having 1 to 3 carbon atoms such as a methyl group, an ethyl group, a propyl group, an isopropyl group and the like; and a straight chained or branched alkylthio group having 1 to 3 carbon atoms in total containing a sulfur atom to be directly bonded to an $M_1$ atom such as a methylthio group, an ethylthio group, an n-propylthio group, iso-propylthio group and the like.

When $Y_1$ is an alkyl group, in the above general formula (1), $Y_1$ is preferably a methyl group.

Further, when $Y_1$ is an alkyl group and d–c is an integer of not less than 2, $Y_1$s may be bonded to each other to form a cyclic structure through the $M_1$ atom. Namely, a plurality of $Y_1$s may be bonded to form a ring containing an $M_1$ atom.

When a ring is formed, examples of the alkyl chain forming the ring include a methylene group, an ethylene group and a propylene group, that is, an alkylene group having 1 to 3 carbon atoms. The alkyl chain forming the ring is preferably an ethylene group.

Incidentally, the ring containing an $M_1$ atom is specifically a 4-membered ring to a 6-membered ring, and an atom constituting the ring may contain, for example, S as described below in addition to $M_1$ and C (carbon).

When $Y_1$ is a thioalkyl group containing a sulfur atom to be directly bonded to an $M_1$ atom, the compound represented by the above general formula (1) is, for example, a compound represented by the following general formula (11),

[Chemical Formula 14]

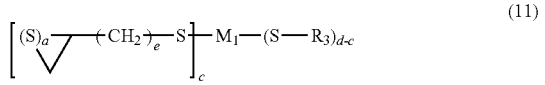

(11)

wherein, in the above general formula (11), $M_1$, a, c, d and e each represent the same as $M_1$, a, c, d and e in the above general formula (1);

when d–c is 1, $R_3$ represents an alkyl group having a straight chain or a branched chain of 1 to 3 carbon atoms which may have a substituent; and when d–c is not less than 2, a plurality of $R_3$s each independently represent an alkyl group having a straight chain or a branched chain of 1 to 3 carbon atoms which may have a substituent or a single bond, and the plurality of $R_3$s may be bonded to each other to form a ring containing an $M_1$ atom, and a portion constituting the ring does not contain a sulfur atom.

In the above general formula (11), $R_3$ represents an alkyl group having a straight chain or a branched chain of 1 to 3 carbon atoms which may have a substituent.

$R_3$s each independently represent an alkyl group having a straight chain or a branched chain of 1 to 3 carbon atoms which may have a substituent. A plurality of $R_3$s may be the same group, or may be groups, a part or all of which are different. Furthermore, a plurality of $R_3$s may be bonded to each other to form a ring containing the atom group —S-$M_1$-S—. In this case, there only exist sulfur atoms, which are directly bonded to the $M_1$ atom. Namely, of $R_3$s, a portion constituting the ring does not contain a sulfur atom.

One of preferable examples of the compound represented by the above general formula (11) includes the following embodiment. That is, when $R_3$s do not form a ring, concrete examples of $R_3$ include a methyl group, an ethyl group, a propyl group and an isopropyl group, that is, an alkyl group having 1 to 3 carbon atoms.

Furthermore, other preferable examples of the compound represented by the above general formula (11) include compounds in which d–c is 2, two —S—$R_3$ groups form a ring containing the atom group —S-$M_1$-S— together with an $M_1$ atom adjacent to S, and the alkyl chain forming the ring is an alkylene group having 1 to 3 carbon atoms. It is preferable that the ring containing an $M_1$ atom is specifically a 4-membered ring to a 6-membered ring. Incidentally, when the ring containing an $M_1$ atom is a 4-membered ring, one of the two $R_3$s is specifically a single bond.

For example, when $R_3$s form a ring, a compound represented by the following general formula (12) can be cited,

[Chemical Formula 15]

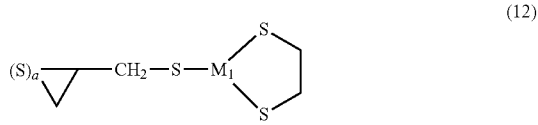

(12)

wherein, in the above general formula (12), a and $M_1$ each represent the same as those in the general formula (11).

Further specifically, it is preferable that, when a ring is not formed, $R_3$ is a methyl group, and when a ring is formed, the alkyl chain forming the ring is an ethylene group.

The compound represented by the general formula (1) as described above is obtained by reacting a halide represented by the following general formula (13) with a compound represented by the following general formula (14),

[Chemical Formula 16]

(13)

wherein, in the above formula (13), c, d, $M_1$ and $Y_1$ each represent the same as those in the general formula (1); and W represents a halogen atom,

[Chemical Formula 17]

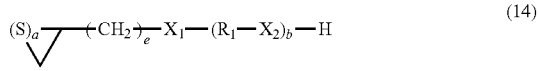

(14)

wherein, in the above formula (14), a, b, e, $X_1$, $X_2$ and $R_1$ each represent the same as those in the general formula (1).

The compounds represented by the above general formula (13) are available as an industrial raw material or a reagent for research purpose.

Furthermore, the compound represented by the above general formula (14) is produced, for example, in accordance with the production method as described in JOURNAL OF THE CHEMICAL SOCIETY, pp. 2660 to 2665 (1960).

The above reaction may be carried out in the absence of a solvent, or may be carried out in the presence of an organic solvent which is inactive to the reaction.

The solvents are not particularly limited as long as they are inactive to the reaction. Examples thereof include hydrocarbon solvents such as petroleum ether, hexane, benzene, toluene, xylene, mesitylene and the like; ether solvents such as diethyl ether, tetrahydrofuran, diethylene glycol dimethyl ether and the like; ketone solvents such as acetone, methyl ethyl ketone, methyl isobutyl ketone and the like; ester solvents such as ethyl acetate, butyl acetate, amyl acetate and the like; chlorine-containing solvents such as methylene chloride, chloroform, chlorobenzene, dichlorobenzene and the like; polar aprotic solvents such as N,N-dimethylformamide, N,N-dimethylacetamide, N,N-dimethylimidazolidinone, dimethyl sulfoxide and the like; sulfur-containing solvents such as tetrahydrothiophene, thiophene, sulfolane, trimethylene sulfide, diethyl sulfide, di-n-propyl sulfide, di-t-butyl sulfide, bis(2-mercaptoethyl)sulfide and the like; water and the like.

The reaction temperature is not particularly limited, but it is usually in the range of from −78 to 200 degrees centigrade and preferably from −78 to 100 degrees centigrade.

Further, the reaction time is affected by the reaction temperature, but it is usually from several minutes to 100 hours.

In the reaction of the compound represented by the above general formula (13) with the compound represented by the above general formula (14), the amounts of the compound represented by the above general formula (13) and the compound represented by the above general formula (14) used are not particularly limited, but the amount of the compound represented by the above general formula (14) is usually not less than 0.01 and not more than 100 mole, preferably not less than 0.1 and not more than 50 mole and more preferably not less than 0.5 and not more than 20 mole, based on 1 mole of the halogen atom contained in the compound represented by the above general formula (13).

The reaction may be carried out in the absence of a catalyst, or may be carried out in the presence of a catalyst.

In order to effectively carry out the reaction, it is preferable to use a base.

Examples of the base include pyridine, triethylamine, dimethylaniline, diethylaniline, 1,8-diazabicyclo[5,4,0]-7-undecene and the like.

Incidentally, as a method for producing the compound of the general formula (12) in which a plurality of $Y_1$s are bonded to form a ring containing an $M_1$ atom, there is a method involving adding the general formula (14) and ethanedithiol dropwise to the general formula (13) in the reaction of the general formula (13) with the general formula (14). Or, ethanedithiol is added dropwise to the product obtained by reacting the general formula (13) with the general formula (14).

Polymerizable Composition

Next, the polymerizable composition of the present invention will be described.

The aforementioned polymerizable composition contains a compound represented by the above general formula (1).

The amount of the compound represented by the above general formula (1) in the polymerizable composition is not particularly restricted. For example, from the viewpoint of improvement in general physical properties such as the mechanical strength, heat resistance and the like of an optical resin composition, the amount may be not less than 1 weight % in the total polymerizable composition.

The polymerizable composition of the present invention may contain at least one of a thiol compound, an isocyanate compound, an episulfide compound (an epithio compound), an epoxy compound, a non-metal thietane compound, a metal thietane compound, a (meth)acrylate ester compound, a vinyl compound and an oxetane compound, in addition to the compound represented by the above general formula (1).

When the polymerizable composition is constructed to contain a compound represented by the above general formula (1), and any of a thiol compound, an epoxy compound, an epithio compound or a thietane compound, mechanical properties and color tone of the obtained resin can be much further enhanced.

Hereinafter, concrete examples of the thiol compound, the epoxy compound, the epithio compound, the non-metal thietane compound and the metal thietane compound will be respectively described. Incidentally, in the following description, when the component of the polymerizable composition in the present invention has a plurality of functional groups, the priority of the functional groups is as follows.

(i) thiol group
(ii) epoxy group
(iii) epithio group
(iv) thietanyl group

For example, in the following, a compound having a thiol group and a thietanyl group will be described in the thiol compound item.

Thiol Compound

Initially, the thiol compound will be described.

The thiol compound used for the polymerizable composition is a compound containing one or more thiol groups (SH groups) in a molecule.

When the polymerizable composition contains the compound represented by the above general formula (1), as the thiol compound, there can also be used, for example, a compound having any structure as long as it is compatible with the compound represented by the above general formula (1).

As the thiol compound, concrete examples of a monovalent thiol compound include aliphatic mercaptan compounds such as methyl mercaptan, ethyl mercaptan, propyl mercaptan, butyl mercaptan, octyl mercaptan, dodecyl mercaptan, tert-dodecyl mercaptan, hexadecyl mercaptan, octadecyl mercaptan, cyclohexyl mercaptan, benzyl mercaptan, ethylphenyl mercaptan, 2-mercaptomethyl-1,3-dithiolane, 2-mercaptomethyl-1,4-dithiane, 1-mercapto-2,3-epithiopropane, 1-mercaptomethylthio-2,3-epithiopropane, 1-mercaptoethylthio-2,3-epithiopropane, 3-mercaptothietane, 2-mercaptothietane, 3-mercaptomethylthiothietane, 2-mercaptomethylthiothietane, 3-mercaptoethylthiothietane, 2-mercaptoethylthiothietane and the like; aromatic mercaptan compounds such as thiophenol, mercaptotoluene and the like; and compounds each containing a hydroxy group in addition to the mercapto group such as 2-mercaptoethanol, 3-mercapto-1,2-propanediol and the like.

Furthermore, examples of the polyhydric thiol (polythiol) compound include aliphatic polythiol compounds such as 1,1-methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, 1,1-bis(mercaptomethyl)cyclohexane, thiomalic acid bis(2-mercaptoethyl ester), 2,3-dimercapto-1-propanol(2-mercaptoacetate), 2,3-dimercapto-1-propanol(3-mercaptopropionate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl)ether, ethylene glycol bis(2-mercaptoacetate), ethylene glycol bis(3-mercaptopropionate), trimethylolpropane bis(2-mercaptoacetate), trimethylolpropane bis(3-mercaptopropionate), pentaerythritol tetrakis(2-mercaptoacetate), pentaerythritol tetrakis(3-mercaptopropionate), tetrakis(mercaptomethyl)methane, 1,1,1,1-tetrakis(mercaptomethyl)methane and the like;

aromatic polythiol compounds such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 2,5-toluenedithiol, 3,4-toluenedithiol, 1,3-di(p-methoxyphenyl)propane-2,2-dithiol, 1,3-diphenylpropane-2,2-dithiol, phenylmethane-1,1-dithiol, 2,4-di(p-mercaptophenyl)pentane and the like;

aromatic polythiol compounds each containing a sulfur atom in addition to the mercapto group such as 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene and the like, and nuclear alkylated products thereof;

aliphatic polythiol compounds each containing a sulfur atom in addition to the mercapto group such as bis(mercaptomethyl)sulfide, bis(mercaptomethyl)disulfide, bis(mercaptoethyl)sulfide, bis(mercaptoethyl)disulfide, bis(mercaptopropyl)sulfide, bis(mercaptomethylthio)methane, bis(2-mercaptoethylthio)methane, bis(3-mercaptopropylthio)methane, 1,2-bis(mercaptomethylthio)ethane, 1,2-bis(2-mercaptoethylthio)ethane, 1,2-bis(3-mercaptopropyl)ethane, 1,3-bis(mercaptomethylthio)propane, 1,3-bis(2-mercaptoethylthio)propane, 1,3-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, 1,2-bis[(2-mercaptoethyl)thio]-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, bis(1,3-dimercaptopropyl)sulfide, 2,5-dimercapto-1,4-dithiane, 2,5-bis(mercaptomethyl)-1,4-dithiane, 2,5-dimercaptomethyl-2,5-dimethyl-1,4-dithiane, bis(mercaptomethyl)disulfide, bis(mercaptoethyl)disulfide, bis(mercaptopropyl)disulfide, 4-mercaptomethyl-1,8-dimercapto-3,6-dithiaoctane and the like, and thioglycolic acid and mercaptopropionic acid esters thereof;

aliphatic polythiol compounds each having an ester bond and a sulfur atom in addition to the mercapto group such as hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxypropyl sulfide bis(2-mercaptoacetate), hydroxypropyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), hydroxypropyl disulfide bis(2-mercaptoacetate), hydroxypropyl disulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), thiodiglycolic acid bis(2-mercaptoethyl ester), thiodipropionic acid bis(2-mercaptoethyl ester), 4,4-thiodibutylic acid bis(2-mercaptoethyl ester), dithiodiglycolic acid bis(2-mercaptoethyl ester), dithiodipropionic acid bis(2-mercaptoethyl ester), 4,4-dithiodibutylic acid bis(2-mercaptoethyl ester), thiodiglycolic acid bis(2,3-dimercaptopropyl ester), thiodipropionic acid bis(2,3-dimercaptopropyl ester), dithioglycolic acid bis(2,3-dimercaptopropyl ester), dithiodipropionic acid bis(2,3-dimercaptopropyl ester) and the like;

heterocyclic compounds each containing a sulfur atom in addition to the mercapto group such as 3,4-thiophenedithiol, 2,5-dimercapto-1,3,4-thiadiazole and the like;

compounds each having a hydroxy group in addition to the mercapto group such as glycerine di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), dipentaerythritol pentakis(3-mercaptopropionate), hydroxymethyl-tris(mercaptoethylthiomethyl)methane, 1-hydroxyethylthio-3-mercaptoethylthiobenzene and the like;

1,1,3,3-tetrakis(mercaptomethylthio)propane, 1,1,2,2-tetrakis(mercaptomethylthio)ethane, 4,6-bis(mercaptomethylthio)-1,3-dithiacyclohexane, 1,1,5,5-tetrakis(mercaptomethylthio)-3-thiapentane, 1,1,6,6-tetrakis(mercaptomethylthio)-3,4-dithiahexane, 2,2-bis(mercaptomethylthio)ethanethiol, 2-(4,5-dimercapto-2-thiapentyl)-1,3-dithiacyclopentane, 2,2-bis(mercaptomethyl)-1,3-dithiacyclopentane, 2,5-bis(4,4-bis(mercaptomethylthio)-2-thiabutyl)-1,4-dithiane, 2,2-bis(mercaptomethylthio)-1,3-propanedithiol, 3-mercaptomethylthio-1,7-dimercapto-2,6-dithiaheptane, 3,6-bis(mercaptomethylthio)-1,9-dimercapto-2,5,8-trithianonane, 4,6-bis(mercaptomethylthio)-1,9-dimercapto-2,5,8-trithianonane, 3-mercaptomethylthio-1,6-dimercapto-2,5-dithiahexane, 2-(2,2-bis(mercaptomethylthio)ethyl)-1,3-dithietane, 1,1,9,9-tetrakis(mercaptomethylthio)-5-(3,3-bis(mercaptomethyl thio)-1-thiapropyl)3,7-dithianonane, tris(2,2-bis(mercaptomethylthio)ethyl)methane, tris(4,4-bis(mercaptomethylthio)-2-thiabutyl)methane, tetrakis(2,2-bis(mercaptomethylthio)ethyl)methane, tetrakis(4,4-bis(mercaptomethylthio)-2-thiabutyl)methane, 3,5,9,11-tetrakis(mercaptomethylthio)-1,13-dimercapto-2,6,8,12-tetrathiamidecane, 3,5,9,11,15,17-hexakis(mercaptomethylthio)-1,19-dimercapto-2,6,8,12,14,18-hexathianonadecane, 9-(2,2-bis(mercaptomethylthio)ethyl)-3,5,13,15-tetrakis(mercaptomethylthio)-1,17-dimercapto-2,6,8,10,12,16-hexathiaheptadecane, 3,4,8,9-tetrakis(mercaptomethylthio)-1,11-dimercapto-2,5,7,10-tetrathiaundecane, 3,4,8,9,13,14-hexakis(mercaptomethylthio)-1,16-dimercapto-2,5,7,10,12,15-hexathiahexadecane, 8-{bis(mercaptomethylthio)methyl}-3,4,12,13-tetrakis(mercaptomethylthio)-1,15-dimercapto-2,5,7,9,11,14-hexathiapentadecane, 4,6-bis{3,5-bis(mercaptomethylthio)-7-mercapto-2,6-dithiaheptylthio}-1,3-dithiane, 4-{3,5-bis(mercaptomethylthio)-7-mercapto-2,6-dithiaheptylthio}-6-mercaptomethylthio-1,3-dithiane, 1,1-bis{4-(6-mercaptomethylthio)-1,3-dithianylthio}-3,3-bis(mercaptomethylthio)propane, 1,3-bis{4-(6-mercaptomethylthio)-1,3-dithianylthio}-1,3-bis(mercaptomethylthio)propane, 1-{4-(6-mercaptomethylthio)-1,3-dithianylthio}-3-{2,2-bis(mercaptomethylthio)ethyl}-7,9-bis(mercaptomethylthio)-2,4,6,10-tetrathiaundecane, 1-{4-(6-mercaptomethylthio)-1,3-dithianylthio}-3-{2-(1,3-dithietanyl)}methyl-7,9-bis(mercaptomethylthio)-2,4,6,10-tetrathiaundecane, 1,5- bis{4-(6-mercaptomethylthio)-1,3-dithianylthio}-3-{2-(1,3-dithietanyl)}methyl-2,4-dithiapentane, 4,6-bis[3-{2-(1,3-dithietanyl)}methyl-5-mercapto-2,4-dithiapentylthio]-1,3-dithiane, 4,6-bis{4-(6-mercaptomethylthio)-1,3-dithianylthio}-1,3-dithiane, 4-{4-(6-mercaptomethylthio)-1,3-dithianylthio}-6-{4-(6-mercaptomethylthio)-1,3-dithianylthio}-1,3-dithiane, 3-{2-(1,3-dithietanyl)}methyl-7,9-bis(mercaptomethylthio)-1,11-dimercapto-2,4,6,10-tetrathiaundecane, 9-{2-(1,3-dithietanyl)}methyl-3,5,13,15-tetrakis(mercaptomethylthio)-1,17-dimercapto-2,6,8,10,12,16-hexathiaheptadecane, 3-{2-(1,3-dithietanyl)}methyl-7,9,13,15-tetrakis(mercaptomethylthio)-1,17-dimercapto-2,4,6,10,12,16-hexathiaheptadecane, 3,7-bis{2-(1,3-dithietanyl)}methyl-1,9-dimercapto-2,4,6,8-tetrathianonane, 4-{3,4,8,9-tetrakis(mercaptomethylthio)-11-mercapto-2,5,7,10-tetrathiaundecyl}-5-mercaptomethylthio-1,3-dithiolane, 4,5-bis{3,4-bis(mercaptomethylthio)-6-mercapto-2,5-dithiahexylthio}-1,3-dithiolane, 4-{3,4-bis(mercaptomethylthio)-6-mercapto-2,5-dithiahexylthio}-5-mercaptomethylthio-1,3-dithiolane, 4-{3-bis(mercaptomethylthio)methyl-5,6-bis(mercaptomethylthio)-8-mercapto-2,4,7-trithiaoctyl}-5-mercaptomethylthio-1,3-dithiolane, 2-[bis{3,4-bis(mercaptomethylthio)-6-mercapto-2,5-dithiahexylthio}methyl]-1,3-dithietane, 2-{3,4-bis(mercaptomethylthio)-6-mercapto-2,5-dithiahexylthio}mercaptomethylthiomethyl-1,3-dithietane, 2-{3,4,8,9-tetrakis(mercaptomethylthio)-11-mercapto-2,5,7,10-tetrathiaundecylthio}mercaptomethylthiomethyl-1,3-dithietane, 2-{3-bis(mercaptomethylthio)methyl-5,6-bis(mercaptomethylthio)-8-mercapto-2,4,7-trithiaoctyl}mercaptomethylthiomethyl-1,3-dithietane, 4,5-bis[1-{2-(1,3-dithietanyl)}-3-mercapto-2-thiapropylthio]-1,3-dithiolane, 4-[1-{2-(1,3-dithietanyl)}-3-mercapto-2-thiapropylthio]-5-{1,2-bis(mercaptomethylthio)-4-mercapto-3-thiabutylthio}-1,3-dithiolane, 2-[bis{4-(5-mercaptomethylthio-1,3-dithioranyl)thio}]methyl-1,3-dithietane, 4-{4-(5-mercaptomethylthio-1,3-dithioranyl)thio}-5-[1-{2-(1,3-dithietanyl)}-3-mercapto-2-thiapropylthio]-1,3-dithiolane, and compounds each having dithioacetal or dithioketal skeleton such as their oligomer and the like;

tris(mercaptomethylthio)methane, tris(mercaptoethylthio)methane, 1,1,5,5-tetrakis(mercaptomethylthio)-2,4-dithiapentane, bis[4,4-bis(mercaptomethylthio)-1,3-dithiabutyl](mercaptomethylthio)methane, tris[4,4-bis(mercaptomethylthio)-1,3-dithiabutyl]methane, 2,4,6-tris(mercaptomethylthio)-1,3,5-trithiacyclohexane, 2,4-bis(mercaptomethylthio)-1,3,5-trithiacyclohexane, 1,1,3,3-tetrakis(mercaptomethylthio)-2-thiapropane, bis(mercaptomethyl)methylthio-1,3,5-trithiacyclohexane, tris[(4-mercaptomethyl-2,5-dithiacyclohexyl-1-yl)methylthio]methane, 2,4-bis(mercaptomethylthio)-1,3-dithiacyclopentane, 2-mercaptoethylthio-4-mercaptomethyl-1,3-dithiacyclopentane, 2-(2,3-dimercaptopropylthio)-1,3-dithiacyclopentane, 4-mercaptomethyl-2-(2,3-dimercaptopropylthio)-1,3-dithiacyclopentane, 4-mercaptomethyl-2-(1,3-dimercapto-2-propylthio)-1,3-dithiacyclopentane, tris[2,2-bis(mercaptomethylthio)-1-thiaethyl]methane, tris[3,3-bis(mercaptomethylthio)-2-thiapropyl]methane, tris[4,4-bis(mercaptomethylthio)-3-thiabutyl]methane, 2,4,6-tris[3,3-bis(mercaptomethylthio)-2-thiapropyl]-1,3,5-trithiacyclohexane, tetrakis[3,3-bis(mercaptomethylthio)-2-thiapropyl]methane, and compounds each having trithio orthoformic ester skeleton such as their oligomer and the like; and 3,3'-di(mercaptomethylthio)-1,5-dimercapto-2,4-dithiapentane, 2,2'-di(mercaptomethylthio)-1,3-dithiacyclopentane, 2,7-di(mercaptomethyl)-1,4,5,9-tetrathiaspiro[4,4]nonane, 3,9-dimercapto-1,5,7,11-tetrathiaspiro[5,5]undecane, compounds each having tetrathio orthocarbonate ester skeleton such as their oligomer and the like, but are not restricted to these exemplified compounds alone. These exemplified compounds may be used singly or two or more compounds may be used in combination.

Of these thiol compounds, in consideration of the optical physical properties of the obtained resin, particularly Abbe's number, it is preferable to select an aliphatic thiol compound rather than an aromatic thiol compound. Furthermore, in consideration of requirements of optical physical properties, particularly refractive index, it is much further preferable to select a compound having a sulfur group in addition to the thiol group such as a sulfide bond and/or a disulfide bond. From the viewpoint of enhancement of 3-dimensional crosslinking property considering the heat resistance of the obtained resin, it is particularly preferable to select one or more thiol compounds having a polymerizable group such as an epithio group, a thietanyl group or the like, or one or more compounds having three or more thiol groups.

From the above viewpoint, preferable examples of the thiol compound include 1-mercapto-2,3-epithiopropane, 1-mercaptomethylthio-2,3-epithiopropane, 1-mercaptoethylthio-2,3-epithiopropane, 3-mercaptothietane, 2-mercaptothietane, 3-mercaptomethylthiothietane, 2-mercaptomethylthiothietane, 3-mercaptoethylthiothietane, 2-mercaptoethylthiothietane, 2,5-bis(mercaptomethyl)-1,4-dithiane, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1,1-tetrakis(mercaptomethyl)methane, 1,1,3,3-tetrakis(mercaptomethylthio)propane, 1,1,2,2-tetrakis(mercaptomethylthio)ethane, 4,6-bis(mercaptomethylthio)-1,3-dithiane and 2-(2,2-bis(mercaptomethylthio)ethyl)-1,3-dithietane.

Further preferable examples thereof include 3-mercaptothietane, 4-mercaptomethyl-1,8-dimercapto-3,6-dithiaoctane, 2,5-bis(mercaptomethyl)-1,4-dithiane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1,1-tetrakis(mercaptomethyl)methane, 1,1,3,3-tetrakis(mercaptomethylthio)propane, 1,1,2,2-tetrakis(mercaptomethylthio)ethane, 4,6-bis(mercaptomethylthio)-1,3-dithiane and 2-(2,2-bis(mercaptomethylthio)ethyl)-1,3-dithietane. Furthermore, when a divalent thiol compound is selected, it is preferable that a thiol compound having a polymerizable group and/or a tri- or higher valent thiol compound are mixed together prior to use.

When the polymerizable composition contains the compound represented by the above general formula (1), the thiol compound is further specifically one or more compounds selected from the group consisting of 3-mercaptothietane, 1,2-ethanedithiol, 4-mercaptomethyl-1,8-dimercapto-3,6-dithiaoctane, 4,8-dimercaptomethyl-1,11-dimercapto-3,6,9-trithiaundecane and 2,5-bis(mercaptomethyl)-1,4-dithiane.

In the polymerizable composition, an isocyanate compound may be further combined in addition to the thiol compound. By adding the isocyanate compound, the mechanical properties or the like are further improved in some cases.

The isocyanate compound to be used herein is not particularly limited, but it is preferably a polyisocyanate compound having a plurality of isocyanate groups, and further preferably a diisocyanate compound. Concrete suitable examples thereof include hexamethylene diisocyanate, bis(isocyanatomethyl)cyclohexane, xylene diisocyanate, dicyclohexylmethane diisocyanate, toluene diisocyanate, 2,5-bis(isocyanatomethyl)bicyclo-[2,2,1]-heptane, 2,6-bis(isocyanatomethyl)bicyclo-[2,2,1]-heptane, isophorone diisocyanate and the like.

Further, a reactant obtained by reacting the thiol compound and the isocyanate compound may be added to the polymerization product in advance.

Epoxy Compound and Epithio Compound

Hereinafter, the epoxy compound and the epithio compound will be described.

The polymerizable composition of the present invention may contain an epoxy compound and/or an epithio compound.

The epoxy compound and the epithio compound each contain one or more epoxy groups and one or more epithio groups in a molecule, and are compounds different from the compound represented by the general formula (1). The epoxy compound and the epithio compound can also be used, for example, for a compound having any structure as long as it is miscible with the compound represented by the above general formula (1), and are each preferably a compound containing two or more epoxy groups and/or epithio groups in total.

Concrete examples of the epoxy resin include a phenol type epoxy compound obtained by the condensation reaction of a polyhydric phenol compound such as bisphenol A, bisphenol F and the like with an epihalohydrin compound (for example, bisphenol A glycidyl ether, bisphenol F glycidyl ether);

an alcohol type epoxy compound obtained by condensation of a polyhydric alcohol compound such as hydrogenated bisphenol A, hydrogenated bisphenol F, cyclohexane dimethanol and the like with an epihalohydrin compound (for example, hydrogenated bisphenol A glycidyl ether, hydrogenated bisphenol F glycidyl ether), and other alcohol type epoxy compounds such as ethylene glycol diglycidyl ether, neopentyl glycol diglycidyl ether, 1,4-cyclohexane dimethanol diglycidyl ether, trimethylolpropane triglycidyl ether and the like;

a glycidyl ester type epoxy compound such as 3,4-epoxycyclohexylmethyl-3',4'-epoxycyclohexane carboxylate, 1,2-hexahydrophthalic acid diglycidyl ester and the like; and an amine type epoxy compound obtained by condensation of primary and secondary amine compounds with an epihalohydrin compound (for example, triglycidyl ether isocyanurate). In addition thereto, an aliphatic polyhydric epoxy compound such as vinylcyclohexene diepoxide including 4-vinyl-1-cyclohexane diepoxide and the like can be cited.

Concrete examples of the epoxy compound having a sulfide group and the epoxy compound having an ether group include chained aliphatic 2,3-epoxypropylthio compounds such as bis(2,3-epoxypropyl)sulfide, bis(2,3-epoxypropyl)disulfide, bis(2,3-epoxypropylthio)methane, 1,2-bis(2,3-epoxypropylthio)ethane, 1,2-bis(2,3-epoxypropylthio)propane, 1,3-bis(2,3-epoxypropylthio)propane, 1,3-bis(2,3-epoxypropylthio)-2-methylpropane, 1,4-bis(2,3-epoxypropylthio)butane, 1,4-bis(2,3-epoxypropylthio)-2-methylbutane, 1,3-bis(2,3-epoxypropylthio)butane, 1,5-bis(2,3-epoxypropylthio)pentane, 1,5-bis(2,3-epoxypropylthio)-2-methylpentane, 1,5-bis(2,3-epoxypropylthio)-3-thiapentane, 1,6-bis(2,3-epoxypropylthio)hexane, 1,6-bis(2,3-epoxypropylthio)-2-methylhexane, 3,8-bis(2,3-epoxypropylthio)-3,6-dithiaoctane, 1,2,3-tris(2,3-epoxypropylthio)propane, 2,2-bis(2,3-epoxypropylthio)-1,3-bis(2,3-epoxypropylthiomethyl)propane, 2,2-bis(2,3-epoxypropylthiomethyl)-1-(2,3-epoxypropylthio)butane, 1,5-bis(2,3-epoxypropylthio)-2-(2,3-epoxypropylthiomethyl)-3-thiapentane, 1,5-bis(2,3-epoxypropylthio)-2,4-bis(2,3-epoxypropylthiomethyl)-3-thiapentane, 1-(2,3-epoxypropylthio)-2,2-bis(2,3-epoxypropylthiomethyl)-4-thiahexane, 1,5,6-tris(2,3-epoxypropylthio)-4-(2,3-epoxypropylthiomethyl)-3-thiahexane, 1,8-bis(2,3-epoxypropylthio)-4-(2,3-epoxypropylthiomethyl)-3,6-dithiaoctane, 1,8-bis(2,3-epoxypropylthio)-4,5-bis(2,3-epoxypropylthiomethyl)-3,6-dithiaoctane, 1,8-bis(2,3-epoxypropylthio)-4,4-bis(2,3-epoxypropylthiomethyl)-3,6-dithiaoctane, 1,8-bis(2,3-epoxypropylthio)-2,5-bis(2,3-epoxypropylthiomethyl)-3,6-dithiaoctane, 1,8-bis(2,3-epoxypropylthio)-2,4,5-tris(2,3-epoxypropylthiomethyl)-3,6-dithiaoctane, 1,1,1-tris[[2-(2,3-epoxypropylthio)ethyl]thiomethyl]-2-(2,3-epoxypropylthio)ethane, 1,1,2,2-tetrakis[[2-(2,3-epoxypropylthio)ethyl]thiomethyl]ethane, 1,11-bis(2,3-epoxypropylthio)-4,8-bis(2,3-epoxypropylthiomethyl)-3,6,9-trithiaundecane, 1,11-bis(2,3-epoxypropylthio)-4,7-bis(2,3-epoxypropylthiomethyl)-3,6,9-trithiaundecane, 1,11-bis(2,3-epoxypropylthio)-5,7-bis(2,3-epoxypropylthiomethyl)-3,6,9-trithiaundecane and the like;

cyclic aliphatic 2,3-epoxypropylthio compounds such as 1,3-bis(2,3-epoxypropylthio)cyclohexane, 1,4-bis(2,3-epoxypropylthio)cyclohexane, 1,3-bis(2,3-epoxypropylthiomethyl)cyclohexane, 1,4-bis(2,3-epoxypropylthiomethyl)cyclohexane, 2,5-bis(2,3-epoxypropylthiomethyl)-1,4-dithiane, 2,5-bis[[2-(2,3-epoxypropylthio)ethyl]thiomethyl]-1,4-dithiane, 2,5-bis(2,3-epoxypropylthiomethyl)-2,5-dimethyl-1,4-dithiane, 3-(2,3-epoxypropylthio)ethane and the like;

aromatic 2,3-epoxypropylthio compounds such as 1,2-bis(2,3-epoxypropylthio)benzene, 1,3-bis(2,3-epoxypropylthio)benzene, 1,4-bis(2,3-epoxypropylthio)benzene, 1,2-bis(2,3-epoxypropylthiomethyl)benzene, 1,3-bis(2,3-epoxypropylthiomethyl)benzene, 1,4-bis(2,3-epoxypropylthiomethyl)benzene, bis[4-(2,3-epoxypropylthio)phenyl]methane, 2,2-bis[4-(2,3-epoxypropylthio)phenyl]propane, bis[4-(2,3-epoxypropylthio)phenyl]sulfide, bis[4-(2,3-epoxypropylthio)phenyl]sulfone, 4,4'-bis(2,3-epoxypropylthio)biphenyl and the like;

monofunctional epoxy compounds such as ethylene oxide, propylene oxide, glycidol, epichlorohydrin and the like;

chained aliphatic 2,3-epoxypropyloxy compounds such as bis(2,3-epoxypropyl)ether, bis(2,3-epoxypropyloxy)methane, 1,2-bis(2,3-epoxypropyloxy)ethane, 1,2-bis(2,3-epoxypropyloxy)propane, 1,3-bis(2,3-epoxypropyloxy)propane, 1,3-bis(2,3-epoxypropyloxy)-2-methylpropane, 1,4-bis(2,3-epoxypropyloxy)butane, 1,4-bis(2,3-epoxypropyloxy)-2-methylbutane, 1,3-bis(2,3-epoxypropyloxy)butane, 1,5-bis(2,3-epoxypropyloxy)pentane, 1,5-bis(2,3-epoxypropyloxy)-2-methylpentane, 1,5-bis(2,3-epoxypropyloxy)-3-thiapentane, 1,6-bis(2,3-epoxypropyloxy)hexane, 1,6-bis(2,3-epoxypropyloxy)-2-methylhexane, 3,8-bis(2,3-epoxypropyloxy)-3,6-dithiaoctane, 1,2,3-tris(2,3-epoxypropyloxy)propane, 2,2-bis(2,3-epoxypropyloxy)-1,3-bis(2,3-epoxypropyloxymethyl)propane, 2,2-bis(2,3-epoxypropyloxymethyl)-1-(2,3-epoxypropyloxy)butane, 1,5-bis(2,3-epoxypropyloxy)-2-(2,3-epoxypropyloxymethyl)-3-thiapentane, 1,5-bis(2,3-epoxypropyloxy)-2,4-bis(2,3-epoxypropyloxymethyl)-3-thiapentane, 1-(2,3-epoxypropyloxy)-2,2-bis(2,3-epoxypropyloxymethyl)-4-thiahexane, 1,5,6-tris(2,3-epoxypropyloxy)-4-(2,3-epoxypropyloxymethyl)-3-thiahexane, 1,8-bis(2,3-epoxypropyloxy)-4-(2,3-epoxypropyloxymethyl)-3,6-dithiaoctane, 1,8-bis(2,3- epoxypropyloxy)-4,5-bis(2,3-epoxypropyloxymethyl)-3,6-dithiaoctane, 1,8-bis(2,3-epoxypropyloxy)-4,4-bis(2,3-epoxypropyloxymethyl)-3,6-dithiaoctane, 1,8-bis(2,3-epoxypropyloxy)-2,5-bis(2,3-epoxypropyloxymethyl)-3,6-dithiaoctane, 1,8-bis(2,3-epoxypropyloxy)-2,4,5-tris(2,3-epoxypropyloxymethyl)-3,6-dithiaoctane, 1,1,1-tris[[2-(2,3-epoxypropyloxy)ethyl]thiomethyl]-2-(2,3-epoxypropyloxy)ethane, 1,1,2,2-tetrakis[[2-(2,3-epoxypropyloxy)ethyl]thiomethyl]ethane, 1,11-bis(2,3-epoxypropyloxy)-4,8-bis(2,3-epoxypropyloxymethyl)-3,6,9-trithiaundecane, 1,11-bis(2,3-epoxypropyloxy)-4,7-bis(2,3-epoxypropyloxymethyl)-3,6,9-trithiaundecane, 1,11-bis(2,3-epoxypropyloxy)-5,7-bis(2,3-epoxypropyloxymethyl)-3,6,9-trithiaundecane and the like;

cyclic aliphatic 2,3-epoxypropyloxy compounds such as 1,3-bis(2,3-epoxypropyloxy)cyclohexane, 1,4-bis(2,3-epoxypropyloxy)cyclohexane, 1,3-bis(2,3-epoxypropyloxymethyl)cyclohexane, 1,4-bis(2,3-epoxypropyloxymethyl)cyclohexane, 2,5-bis(2,3-epoxypropyloxymethyl)-1,4-dithiane, 2,5-bis[[2-(2,3-epoxypropyloxy)ethyl]thiomethyl]-1,4-dithiane, 2,5-bis(2,3-epoxypropyloxymethyl)-2,5-dimethyl-1,4-dithiane and the like; and aromatic 2,3-epoxypropyloxy compounds such as 1,2-bis(2,3-epoxypropyloxy)benzene, 1,3-bis(2,3-epoxypropyloxy)benzene, 1,4-bis(2,3-epoxypropyloxy)benzene, 1,2-bis(2,3-epoxypropyloxymethyl)benzene, 1,3-bis(2,3-epoxypropyloxymethyl)benzene, 1,4-bis(2,3-epoxypropyloxymethyl)benzene, bis[4-(2,3-epoxypropyloxy)phenyl]methane, 2,2-bis[4-(2,3-epoxypropyloxy)phenyl]propane, bis[4-(2,3-epoxypropyloxy)phenyl]sulfide, bis[4-(2,3-epoxypropyloxy)phenyl]sulfone, 4,4'-bis(2,3-epoxypropyloxy)biphenyl and the like, but are not restricted to these exemplified compounds alone.

Of these exemplified epoxy compounds, preferable examples include bis(2,3-epoxypropyl)disulfide; 4-vinyl-1-cyclohexane diepoxide; a phenol type epoxy compound such as bisphenol A glycidyl ether, bisphenol F glycidyl ether and the like;

an alcohol type epoxy compound such as hydrogenated bisphenol A glycidyl ether, hydrogenated bisphenol F glycidyl ether, ethylene glycol diglycidyl ether, neopentyl glycol diglycidyl ether, 1,4-cyclohexane dimethanol diglycidyl ether, trimethylolpropane triglycidyl ether and the like;

a glycidyl ester type epoxy compound such as 3,4-epoxycyclohexylmethyl-3',4'-epoxycyclohexane carboxylate, 1,2-hexahydrophthalic acid diglycidyl ester and the like; and an amine type epoxy compound such as triglycidyl ether isocyanurate and the like. In addition thereto, an aliphatic polyhydric epoxy compound such as vinylcyclohexene diepoxide and the like can be cited.

More preferable examples of the epoxy compound include bis(2,3-epoxypropyl)disulfide, 1,4-cyclohexane dimethanol diglycidyl ether, bisphenol A glycidyl ether, bisphenol F glycidyl ether, ethylene glycol diglycidyl ether, neopentyl glycol diglycidyl ether, trimethylolpropane triglycidyl ether and triglycidyl ether isocyanurate. Further preferable examples thereof include 1,4-cyclohexane dimethanol diglycidyl ether and bisphenol F glycidyl ether.

Concrete examples of the epithio compound include epithioethylthio compounds such as bis(1,2-epithioethyl)sulfide, bis(1,2-epithioethyl)disulfide, bis(epithioethylthio)methane, bis(epithioethylthio)benzene, bis[4-(epithioethylthio)phenyl]sulfide, bis[4-(epithioethylthio)phenyl]methane and the like;

chained aliphatic 2,3-epithiopropylthio compounds such as bis(2,3-epithiopropyl)sulfide, bis(2,3-epithiopropyl)disulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 3,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl)propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl)-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris[[2-(2,3-epithiopropylthio)ethyl]thiomethyl]-2-(2,3-epithiopropylthio)ethane, 1,1,2,2-tetrakis[[2-(2,3-epithiopropylthio)ethyl]thiomethyl]ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane, 1,11-bis(2,3-epithiopropylthio)-5,7-bis(2,3-epithiopropylthiomethyl)-3,6,9-trithiaundecane and the like;

cyclic aliphatic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis[[2-(2,3-epithiopropylthio)ethyl]thiomethyl]-1,4-dithiane, 2,5-bis(2,3-epithiopropylthiomethyl)-2,5-dimethyl-1,4-dithiane and the like;

aromatic 2,3-epithiopropylthio compounds such as 1,2-bis(2,3-epithiopropylthio)benzene, 1,3-bis(2,3-epithiopropylthio)benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl]sulfide, bis[4-(2,3-epithiopropylthio)phenyl]sulfone, 4,4'-bis(2,3-epithiopropylthio)biphenyl and the like;

compounds each having one epithio group such as ethylene sulfide, propylene sulfide, mercaptopropylene sulfide, mercaptobutene sulfide, epithiochlorohydrin and the like;

chained aliphatic 2,3-epithiopropyloxy compounds such as bis(2,3-epithiopropyl)ether, bis(2,3-epithiopropyloxy)methane, 1,2-bis(2,3-epithiopropyloxy)ethane, 1,2-bis(2,3-epithiopropyloxy)propane, 1,3-bis(2,3-epithiopropyloxy)propane, 1,3-bis(2,3-epithiopropyloxy)-2-methylpropane, 1,4-bis(2,3-epithiopropyloxy)butane, 1,4-bis(2,3-epithiopropyloxy)-2-methylbutane, 1,3-bis(2,3-epithiopropyloxy)butane, 1,5-bis(2,3-epithiopropyloxy)pentane, 1,5-bis(2,3-epithiopropyloxy)-2-methylpentane, 1,5-bis(2,3- epithiopropyloxy)-3-thiapentane, 1,6-bis(2,3-epithiopropyloxy)hexane, 1,6-bis(2,3-epithiopropyloxy)-2-methylhexane, 3,8-bis(2,3-epithiopropyloxy)-3,6-dithiaoctane, 1,2,3-tris(2,3-epithiopropyloxy)propane, 2,2-bis(2,3-epithiopropyloxy)-1,3-bis(2,3-epithiopropyloxymethyl)propane, 2,2-bis(2,3-epithiopropyloxymethyl)-1-(2,3-epithiopropyloxy)butane, 1,5-bis(2,3-epithiopropyloxy)-2-(2,3-epithiopropyloxymethyl)-3-thiapentane, 1,5-bis(2,3-epithiopropyloxy)-2,4-bis(2,3-epithiopropyloxymetyl)-3-thiapentane, 1-(2,3-epithiopropyloxy)-2,2-bis(2,3-epithiopropyloxymethyl)-4-thiahexane, 1,5,6-tris(2,3-epithiopropyloxy)-4-(2,3-epithiopropyloxymethyl-3-thiahexane, 1,8-bis(2,3-epithiopropyloxy)-4-(2,3-epithiopropyloxymethyl)-3,6-dithiaoctane, 1,8-bis(2,3-epithiopropyloxy)-4,5-bis(2,3-epithiopropyloxymethyl)-3,6-dithiaoctane, 1,8-bis(2,3-epithiopropyloxy)-4,4-bis(2,3-epithiopropyloxymethyl)-3,6-dithiaoctane, 1,8-bis(2,3-epithiopropyloxy)-2,5-bis(2,3-epithiopropyloxymethyl)-3,6-dithiaoctane, 1,8-bis(2,3-epithiopropyloxy)-2,4,5-tris(2,3-epithiopropyloxymethyl)-3,6-dithiaoctane, 1,1,1-tris[[2-(2,3-epithiopropyloxy)ethyl]thiomethyl]-2-(2,3-epithiopropyloxy)ethane, 1,1,2,2-tetrakis[[2-(2,3-epithiopropyloxy)ethyl]thiomethyl]ethane, 1,11-bis(2,3-epithiopropyloxy)-4,8-bis(2,3-epithiopropyloxymethyl)-3,6,9-trithiaundecane, 1,11-bis(2,3-epithiopropyloxy)-4,7-bis(2,3-epithiopropyloxymethyl)-3,6,9-trithiaundecane, 1,11-bis(2,3-epithiopropyloxy)-5,7-bis(2,3-epithiopropyloxymethyl)-3,6,9-trithiaundecane and the like;

cyclic aliphatic 2,3-epithiopropyloxy compounds such as 1,3-bis(2,3-epithiopropyloxy)cyclohexane, 1,4-bis(2,3-epithiopropyloxy)cyclohexane, 1,3-bis(2,3-epithiopropyloxymethyl)cyclohexane, 1,4-bis(2,3-epithiopropyloxymethyl)cyclohexane, 2,5-bis(2,3-epithiopropyloxymethyl)-1,4-dithiane, 2,5-bis[[2-(2,3-epithiopropyloxy)ethyl]thiomethyl]-1,4-dithiane, 2,5-bis(2,3-epithiopropyloxymethyl)-2,5-dimethyl-1,4-dithiane and the like; and aromatic 2,3-epithiopropyloxy compounds such as 1,2-bis(2,3-epithiopropyloxy)benzene, 1,3-bis(2,3-epithiopropyloxy)benzene, 1,4-bis(2,3-epithiopropyloxy)benzene, 1,2-bis(2,3-epithiopropyloxymethyl)benzene, 1,3-bis(2,3-epithiopropyloxymethyl)benzene, 1,4-bis(2,3-epithiopropyloxymethyl)benzene, bis[4-(2,3-epithiopropyloxy)phenyl]methane, 2,2-bis[4-(2,3-epithiopropyloxy)phenyl]propane, bis[4-(2,3-epithiopropyloxy)phenyl]sulfide, bis[4-(2,3-epithiopropyloxy)phenyl]sulfone, 4,4'-bis(2,3-epithiopropyloxy)biphenyl and the like, but are not restricted to these exemplified compounds alone.

Of these exemplified compounds, preferable examples of the compound include bis(1,2-epithioethyl)sulfide, bis(1,2-epithioethyl)disulfide, bis(2,3-epithiopropyl)sulfide, bis(2,3-epithiopropylthio)methane and bis(2,3-epithiopropyl)disulfide. More preferable examples thereof include bis(1,2-epithioethyl)sulfide, bis(1,2-epithioethyl)disulfide, bis(2,3-epithiopropyl)sulfide and bis(2,3-epithiopropyl)disulfide. Further more preferable examples thereof include bis(2,3-epithiopropyl)sulfide and bis(2,3-epithiopropyl)disulfide.

Any one of the epoxy compound and/or the epithio compound can be used or both compounds can be used in combination. The amount ratio is not particularly limited. Furthermore, a plurality of epoxy compounds or different epoxy compounds, or a plurality of epithio compounds or different epithio compounds can also be used together. However, in order to obtain a resin having a high refractive index, it is preferable to use epithio compounds.

Non-Metal Thietane Compound

Hereinafter, the non-metal thietane compound will be described.

The non-metal thietane compound contains one or more thietanyl groups in a molecule. Furthermore, the non-metal thietane compound can also be used, for example, for a compound having any structure as long as it is miscible with the compound represented by the above general formula (1), and is preferably a compound containing two or more thietanyl groups in total.

Concrete examples of the thietane compound include sulfide type thietane compounds such as bisthietanyl sulfide, bis(thietanylthio)methane, 3-(((thietanylthio)methylthio)methylthio)thietane and the like; and polysulfide type thietane compounds such as bisthietanyl disulfide, bisthietanyl trisulfide, bisthietanyl tetrasulfide, bisthietanyl pentasulfide and the like.

Furthermore, as the non-metal thietane compound, a compound represented by the following formula (15) (1,3-bis(thietanylthio)-2-propanol) may be used.

[Chemical Formula 18]

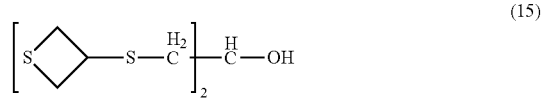

(15)

Of these exemplified compounds, it is preferable to select one or more compounds selected from the group consisting of bisthietanyl disulfide, bisthietanyl tetrasulfide, bis(thietanylthio)methane and 3-(((thietanylthio)methylthio)methylthio)thietane.

Further, of these exemplified compounds, preferable examples of the compound include bisthietanyl sulfide, bis(thietanylthio)methane, bisthietanyl disulfide and bisthietanyl tetrasulfide, and a more preferable example of the compound includes bisthietanyl disulfide.

Further, when the polymerizable composition contains the compound represented by the above general formula (1), a concrete example of combination with other polymerizable compounds includes a combination in which the thiol compound is one or more compounds selected from the group consisting of 3-mercaptothietane, 1,2-ethanedithiol, 4-mercaptomethyl-1,8-dimercapto-3,6-dithiaoctane, 4,8-dimercaptomethyl-1,11-dimercapto-3,6,9-trithiaundecane and 2,5-bis(mercaptomethyl)-1,4-dithiane, the epoxy compound is one or more compounds selected from the group consisting of bis(2,3-epoxypropyl)disulfide, ethylene glycol diglycidyl ether, triglycidyl ether isocyanurate, neopentyl glycol diglycidyl ether, 1,4-cyclohexane dimethanol diglycidyl ether, trimethylolpropane triglycidyl ether, bisphenol F diglycidyl ether, bisphenol A diglycidyl ether and 3,4-epoxycyclohexylmethyl-3',4'-epoxycyclohexane carboxylate, the epithio compound is one or more compounds selected from the group consisting of bis(2,3-epithiopropyl)sulfide and bis(2,3-epithiopropyl)disulfide, and the non-metal thietane compound is one or more compounds selected from the group consisting of bisthietanyl disulfide, bisthietanyl tetrasulfide, bis(thietanylthio)methane and 3-(((thietanylthio)methylthio)methylthio)thietane.

Metal Thietane

As a compound contained in the polymerizable composition according to the present invention, for example, a metal thietane compound represented by the following general formula (3) may be contained.

This metal thietane compound is a compound having a thietane group and a specific metal atom in a molecule. Hereinafter, the compound represented by the following general formula (3) will be illustrated as an example. This polymerizable composition is used, for example, as a material of optical components.

[Chemical Formula 19]

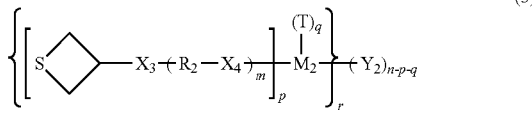

(3)

wherein, in the above general formula (3), $M_2$ represents a metal atom; $X_3$ and $X_4$ each independently represent a sulfur atom or an oxygen atom; $R_2$ represents a divalent organic group;

m represents a number of 0 or an integer of not less than 1;

n represents a valence of M; p represents an integer of not less than 1 and not more than n;

q represents a number of 0 or an integer of not less than 1 and not more than n−2;

$Y_2$ represents a monovalent or divalent group; T represents an inorganic or organic group;

r represents a number of 1 or 2;

when r is 1, $Y_2$ represents a monovalent inorganic or organic group, provided that r is 1 and n−p−q is not less than 2, a plurality of $Y_2$s each independently represent a monovalent inorganic or organic group, and provided that r is 1 and n−p−q is not less than 2, a plurality of $Y_2$s may be bonded to each other to form a ring containing a metal atom $M_2$;

when r is 2 and n−p−q is 1 or 2, $Y_2$ represents a divalent group, provided that r is 2 and n−p−q is 2, two Ys may form a ring along with two metal atoms $M_2$s, and provided that r is 2 and q is 2, a plurality of Ts each independently represent an inorganic or organic group.

The polymerizable composition according to the present invention may contain one compound as the metal thietane compound represented by the above general formula (3), or may contain a plurality of different compounds.

For example, the polymerizable composition may contain a compound in which $M_2$ is Sb (antimony) or Sn (tin) in the above general formula (3) as a metal thietane compound.

Furthermore, the polymerizable composition may contain a plurality of compounds in which metal atoms $M_2$s are different as the metal thietane compound. In this case, the polymerizable composition may contain, for example, a compound in which $M_2$ is Sb and a compound in which $M_2$ is Sn in the above general formula (3) as the metal thietane compound.

Furthermore, from the viewpoint of high refractive index, $X_3$ and $X_4$ in the general formula (3) are each preferably a sulfur atom. In the general formula (3), m=0 is preferable, and r=1 and q=0 are further preferable. m=0, r=1 and q=0 are further preferable, while $X_3$ is particularly preferably sulfur.

Examples of $Y_2$ represent the same as those of $Y_1$, while examples of $R_2$ represent the same as those of $R_1$.

Hereinafter, concrete examples of the compound represented by the above general formula (3) are as follows.

Concrete examples of the metal thietane compound in which $M_2$ is Sn include alkylthio(thietanylthio)tin such as methylthio tris(thietanylthio)tin, ethylthio tris(thietanylthio)tin, propylthio tris(thietanylthio)tin, isopropylthio tris(thietanylthio)tin and the like; bis(alkylthio)bis(thietanylthio)tin such as bis(methylthio)bis(thietanylthio)tin, bis(ethylthio)bis(thietanylthio)tin, bis(propylthio)bis(thietanylthio)tin, bis(isopropylthio)bis(thietanylthio)tin and the like;

alkylthio(alkylthio)bis(thietanylthio)tin such as ethylthio (methylthio)bis(thietanylthio)tin, methylthio(propylthio)bis (thietanylthio)tin, isopropylthio(methylthio)bis(thietanylthio)tin, ethylthio(propylthio)bis(thietanylthio)tin, ethylthio(isopropylthio)bis(thietanylthio)tin, isopropylthio (propylthio)bis(thietanylthio)tin and the like;

bis(thietanylthio)cyclic dithiotin compounds such as bis (thietanylthio)dithiastannetane, bis(thietanylthio)dithiastannolane, bis(thietanylthio)dithiastanninane, bis(thietanylthio) trithiastannocane and the like;

alkyl(thietanylthio)tin compounds such as methyltris(thietanylthio)tin, dimethylbis(thietanylthio)tin, butyltris(thietanylthio)tin and the like; and tetrakis(thietanylthio)tin, but are not restricted to these exemplified compounds alone.

Of these exemplified compounds, preferable examples of the compound include methylthio tris(thietanylthio)tin, bis (thietanylthio)dithiastannetane, bis(thietanylthio)dithiastannolane, bis(thietanylthio)dithiastanninane, bis(thietanylthio) trithiastannocane, methyltris(thietanylthio)tin and tetrakis (thietanylthio)tin. A further preferable example thereof includes tetrakis(thietanylthio)tin.

Concrete examples of the metal thietane compound in which $M_2$ is Sb include alkylthio(thietanylthio)antimony such as methylthio bis(thietanylthio)antimony, ethylthio bis (thietanylthio)antimony, propylthio bis(thietanylthio)antimony, isopropylthio bis(thietanylthio)antimony and the like;

alkylthio tetra(thietanylthio)antimony such as methylthio tetra(thietanylthio)antimony, ethylthio tetra(thietanylthio) antimony, propylthio tetra(thietanylthio)antimony, isopropylthio tetra(thietanylthio)antimony and the like;

bis(alkylthio)(thietanylthio)antimony such as bis(methylthio)(thietanylthio)antimony, bis(ethylthio)(thietanylthio) antimony, bis(propylthio)(thietanylthio)antimony, bis(isopropylthio)(thietanylthio)antimony and the like;

bis(alkylthio)tris(thietanylthio)antimony such as bis(methylthio)tris(thietanylthio)antimony, bis(ethylthio)tris(thietanylthio)antimony, bis(propylthio)tris(thietanylthio)antimony, bis(isopropylthio)tris(thietanylthio)antimony and the like;

tris(alkylthio)bis(thietanylthio)antimony such as tris(methylthio)bis(thietanylthio)antimony, tris(ethylthio)bis(thietanylthio)antimony, tris(propylthio)bis(thietanylthio)antimony, tris(isopropylthio)bis(thietanylthio)antimony and the like;

tetra(alkylthio)(thietanylthio)antimony such as tetra(methylthio)(thietanylthio)antimony, tetra(ethylthio)(thietanylthio)antimony, tetra(propylthio)(thietanylthio)antimony, tetra(isopropylthio)(thietanylthio)antimony and the like;

alkylthio(alkylthio)(thietanylthio)antimony such as ethylthio (methylthio)(thietanylthio)antimony, methylthio(propylthio)(thietanylthio)antimony, isopropylthio (methylthio) (thietanylthio)antimony, ethylthio(propylthio)(thietanylthio) antimony, ethylthio (isopropylthio)(thietanylthio)antimony, isopropylthio(propylthio)(thietanylthio)antimony and the like;

cyclic dithio antimony compounds such as thietanylthio dithiastibetane, thietanylthio dithia stiborane, thietanylthio dithiastibinane, thietanylthio trithia stibocane, tris(thietanylthio)dithia stibetane, tris(thietanylthio)dithiastiborane, tris(thietanylthio)dithia stibinane, bis(thietanylthio)trithia stibocane, tris(thietanylthio)trithiastibocane and the like;

alkyl(thietanylthio)antimony compounds such as methylbis(thietanylthio)antimony, dimethyl(thietanylthio)antimony, butylbis(thietanylthio)antimony and the like;

tris(thietanylthio)antimony, pentakis(thietanylthio)antimony and the like, but are not restricted to these exemplified compounds alone.

Of these exemplified compounds, preferable examples of the compound include methylthio bis(thietanylthio)antimony, thietanylthio dithia stibetane, thietanylthio dithiathiastiborane, thietanylthio dithia stibinane, bis(thietanylthio) trithia stibocane, methylbis(thietanylthio)antimony and tris (thietanylthio)antimony. A further preferable example of the compound includes tris(thietanylthio)antimony.

In the compound represented by the above general formula (3), n=p is preferable. Concrete examples thereof include compounds in which n and p are each 3, while further concrete examples include compounds represented by the following formula (4),

[Chemical Formula 20]

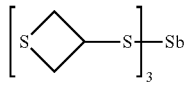

(4)

Concrete examples of the compound represented by the above general formula (3) include compounds in which n and p are each 4, while further concrete examples include compounds represented by the following formula (5),

[Chemical Formula 21]

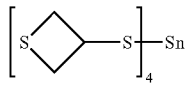

(5)

Next, as a method for producing a metal thietane compound used in the present invention, a method for producing a metal thietane compound represented by the above general formula (3) will be described as an example.

Firstly, a case in which r is 1 in the above general formula (3) will be described. At this time, the above general formula (3) becomes the following general formula (16),

[Chemical Formula 22]

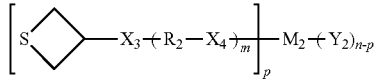

(16)

wherein, in the general formula (16), n, m, p, $X_3$, $R_2$, $X_4$, $M_2$ and $Y_2$ each represent the same as n, m, p, $X_3$, $R_2$, $X_4$, $M_2$ and $Y_2$ in the general formula (3).

The metal thietane compound represented by the above general formula (16) is typically produced by the reaction of a halide containing a metal atom represented by the following general formula (17) with a hydroxy compound or a thiol compound having a thietane group represented by the following general formula (18),

[Chemical Formula 23]

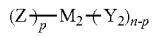

(17)

wherein, in the above general formula (17), n, p, $M_2$ and $Y_2$ each represent the same as n, p, $M_2$ and $Y_2$ in the above general formula (16); and Z represents a halogen atom,

[Chemical Formula 24]

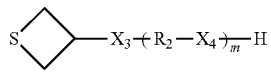

(18)

wherein, in the above general formula (18), $X_3$, $X_4$, $R_2$ and m each represent the same as $X_3$, $X_4$, $R_2$ and m in the above general formula (16).

Incidentally, the metal thietane compound represented by the above general formula (16) can also be produced in accordance with a method other than the method using a metal halide. For example, the metal thietane compound represented by the above general formula (16) can also be produced by reacting the compound represented by the above general formula (18) using a metal oxide or a metal amide as a raw material.

The compound represented by the above general formula (17) is available as an industrial raw material or a reagent for research purpose.

Furthermore, the compound represented by the above general formula (18) is known in the art, and is prepared in accordance with a method as described, for example, in Patent Document 2 (Japanese Patent Laid-Open No. 2003-327583).

The reaction of a halide represented by the above general formula (17) and a hydroxy compound or a thiol compound having a thietane group represented by the above general formula (18) may be carried out in the absence of a solvent or may be carried out in the presence of a solvent which is inactive to the reaction.

The solvents are not particularly limited as long as they are inactive to the reaction. Examples thereof include hydrocarbon solvents such as petroleum ether, hexane, benzene, toluene, xylene, mesitylene and the like; ether solvents such as diethyl ether, tetrahydrofuran, diethylene glycol dimethyl ether and the like; ketone solvents such as acetone, methyl ethyl ketone, methyl isobutyl ketone and the like; ester solvents such as ethyl acetate, butyl acetate, amyl acetate and the like; chlorine-containing solvents such as methylene chloride, chloroform, chlorobenzene, dichlorobenzene and the like; polar aprotic solvents such as N,N-dimethylformamide, N,N-dimethylacetamide, N,N-dimethylimidazolidinone, dimethyl sulfoxide and the like; sulfur-containing solvents such as tetrahydrothiophene, thiophene, sulfolane, trimethylene sulfide, diethyl sulfide, di-n-propyl sulfide, di-t-butyl sulfide, bis(2-mercaptoethyl)sulfide and the like; water and the like.

The temperature for the reaction of the compound represented by the above general formula (17) with the compound represented by the above general formula (18) is not particularly limited, but it is usually in the range of −78 to 200 degrees centigrade and preferably in the range of −78 to 100 degrees centigrade.

The reaction time is affected by the reaction temperature, but it is usually from several minutes to 100 hours.

In the reaction of the compound represented by the above general formula (17) with the compound represented by the above general formula (18), the amounts of the compound represented by the above general formula (17) and the compound represented by the above general formula (18) used are not particularly limited, but the amount of the compound represented by the above general formula (18) is usually not less than 0.01 and not more then 100 mole, preferably not less than 0.1 and not more than 50 mole and more preferably not less than 0.5 and not more than 20 mole, based on 1 mole of the halogen atom contained in the compound represented by the above general formula (17).

When the reaction of the compound represented by the above general formula (17) with the compound represented by the above general formula (18) is carried out, it is preferable to use a basic compound as a capturing agent of the generated halogenated hydrogen in order to effectively carry out the reaction.

Examples of the basic compound include inorganic bases such as sodium hydroxide, potassium hydroxide, lithium hydroxide, sodium carbonate, potassium carbonate, lithium carbonate, sodium bicarbonate, potassium bicarbonate, lithium bicarbonate, magnesium hydroxide, calcium hydroxide and the like; and organic bases such as pyridine, triethylamine, dimethylaniline, diethylaniline, 1,8-diazabicyclo[5,4,0]-7-undecene and the like.

In the above general formula (3), the compound in which r is 2 can be obtained in accordance with the aforementioned method for the compound in which r is 1.

The metal thietane compound represented by the above general formula (3) is a polymerizable compound. Therefore, the polymerizable composition of the present invention may be constructed such that the compounds represented by the above general formulae (1) and (3) are each contained as a polymerizable compound, and the polymerizable compound is mainly composed of the metal thietane compound represented by the above formula (3). For example, the polymerizable compound in the polymerizable composition of the present invention may be constructed to have the metal thietane compound represented by the above formula (5) as a main ingredient.

When the polymerizable compound in the polymerizable composition of the present invention contains the metal thietane compound represented by the above general formula (3), it may contain other polymerizable compounds in addition to the metal thietane compound represented by the above general formula (3). For example, the polymerizable compound in the polymerizable composition of the present invention may contain other polymerizable compounds in addition to the metal thietane compound represented by the above general formula (5).

Examples of other polymerizable compounds contained in the polymerizable composition of the present invention include various known polymerizable monomers or polymerizable oligomers, for example, (meth)acrylic ester compounds, vinyl compounds, oxetane compounds and the like.

Furthermore, the polymerizable composition of the present invention may further contain, if necessary, a known or publicly used polymerization catalyst in order to control the polymerization rate.

Furthermore, the polymerizable composition of the present invention may contain, if necessary, a bluing agent. The bluing agent has an absorption band in an orange-yellow wavelength range of the visible light region, and has a function of adjusting the color tone of the resin. The bluing agent further specifically contains a substance exhibiting colors from blue to violet.

The bluing agent used for the polymerizable composition of the present invention is not particularly limited, and concrete examples thereof include a dye, a fluorescent whitening agent, a fluorescent pigment, an inorganic pigment and the like. The bluing agent is suitably selected from those which can be used as a bluing agent according to the physical properties required for a lens, the color tone of the resin or the like. These bluing agents may be used singly or in combination of two or more kinds.

Of these bluing agents, a dye is preferred from the viewpoints of the solubility into the polymerizable composition and the transparency of the obtained resin. Of dyes, preferably used is a dye containing one or two or more kinds selected from blue based dyes and violet based dyes, but it may be mixed with other color based dyes depending on the situation. For example, gray, brown, red and orange based dyes can also be used in addition to the blue and violet based dyes. Concrete examples of a combination of such bluing agents include a combination of a blue based dye with a red based dye, a combination of a violet based dye with a red based dye, and the like.

From the viewpoint of the absorption wavelength, the maximum absorption wavelength of the dye is preferably not less than 520 and not more than 600 nm and further preferably not less than 540 and not more than 580 nm.

From the viewpoint of the structure of the compound, an anthraquinone based dye is preferable.

Concrete examples of the dye include PS Blue RR, PS Violet RC, PET Blue 2000, PS Brilliant Red HEY, MLP RED V-1 (product names manufactured by DyStar Japan Ltd.) and the like.

The amount of the bluing agent used is different depending on the kind of monomer, existence of various additives in use, the kind and amount of additives in use, the polymerization method or polymerization conditions. The amount is generally not less than 0.001 and not more than 500 ppm, preferably not less than 0.005 and not more than 100 ppm and further preferably not less than 0.01 and not more than 10 ppm, based on the total amount of monomers, namely, the total weight of the polymerizable compound contained in the polymerizable composition. When the amount of the bluing agent added is excessively high, the entire lens becomes excessively blue in some cases; therefore, it is not preferable. Further, when it is excessively small, the effect of improvement of color tone is not fully exhibited in some cases; therefore, it is not preferable.

A method for adding a bluing agent is not particularly limited, and the bluing agent is preferably added to monomers in advance. As a method, there can be adopted various methods such as a method including dissolving the bluing agent in a monomer, or a method including preparing a master solution containing a high density bluing agent and adding it by diluting with a monomer using the master solution or other additives.

Furthermore, in some cases, in order to obtain a good resin, a method or operation generally used for synthesizing an organic compound, such as purification, cleaning, hot insulation, cold insulation, filtration, reduced-pressure treatment or the like is preferably performed for the polymerizable composition of the present invention, or a known compound is preferably added as a stabilizer or a resin modifier for improving a resin and handling property, for example, for controlling the optical physical properties such as the refractive index, Abbe's number and the like, physical properties such as hue, light resistance, weather resistance, heat resistance, impact resistance, hardness, specific gravity, linear expansion coefficient, polymerization shrinkability, water absorption, hygroscopicity, chemical resistance, viscoelasticity and the like, and transmittance and transparency of a resin produced by curing the polymerizable composition, and controlling the viscosity of the polymerizable composition, and preservation and transport handling property. Examples of the compound added for improving stability such as long-term preservation stability, polymerization stability and thermal stability include a polymerization retardant, a polymerization inhibitor, a deoxidant, an antioxidant and the like.

Purification of the polymerizable composition is a means used for improving the transparency of the resin obtained by curing, improving the color tone or increasing the purity of the resin. As a method for purifying the polymerizable composition of the present invention, any known method, for example, recrystallization, column chromatography (a silica gel method, an activated carbon method, an ion-exchange resin method or the like), extraction or the like, may be performed with any timing as long as the transparency and color tone of the resin obtained by curing the purified composition are generally improved.

A method for cleaning the polymerizable composition is a means used for improving the transparency and color tone of the resin obtained by curing. Such a method may be conducted at timing when or after the synthesized polymerizable composition is taken out. In this method, the composition is washed with a polar and/or nonpolar solvent to remove or reduce a resin transparency inhibitor, for example, an inorganic salt used for synthesizing the polymerizable composition or by-produced in synthesizing the composition, such as an ammonium salt or the like. Although the solvent used depends on the polymerizable composition to be cleaned and the polarity of a solution containing the polymerizable composition, and is not limited, a solvent which can dissolve a component to be removed, and which is hardly compatible with the polymerizable composition to be cleaned and the solution containing the polymerizable composition is preferably used. The solvent may be used singly, or a mixture of two or more solvents may be used. Although the amount of a component to be removed depends on the purpose and application, the amount is preferably as low as possible. The amount is usually not more than 5,000 ppm and more preferably not more than 1,000 ppm. In this case, good results are produced in some cases.

A hot insulation, cold insulation or filtration method for the polymerizable composition is a means used for improving the transparency or color tone of the resin obtained by curing. Such a method is generally conducted at timing when or after the synthesized polymerizable composition is taken out. In the hot insulation method, for example, when the polymerizable composition is crystallized to deteriorate handling property during storage, the polymerizable composition is melted by heating within a range causing no deterioration in the performance of the polymerizable composition and the resin obtained by curing the polymerizable composition. Although the heating temperature range and heat melting method depend on the structure of the compound constituting the polymerizable composition to be handled and are not limited, the heating temperature is generally in a range of the solidification point+50 degrees centigrade and preferably the solidification point+20 degrees centigrade. In this method, the composition may be melted by mechanically stirring with a stirring device or bubbling with an inert gas for moving an internal liquid. The cold insulation method is generally performed for improving the preservation stability of the polymerizable composition. However, when the polymerizable composition has a high melting point, consideration may be given to the storage temperature to improve handling property after crystallization. Although the cold insulation temperature depends on the structure and preservation stability of the compound constituting the polymerizable composition to be handled and is not limited, the polymerizable composition of the present invention needs to be stored at a temperature or below which can maintain the stability thereof.

The polymerizable composition of the present invention used for optical applications is required to have excessively high transparency, and thus the polymerizable composition may be usually filtered with a filter having a small pore size. Although the pore size of the filter used herein is usually not less than 0.05 µm and not more than 10 µm, the pore size is preferably not less than 0.05 µm and not more than 5 µm and more preferably not less than 0.1 µm and not more than 5 µm from the viewpoints of operationality and performance. In many cases, filtration of the polymerizable composition of the present invention produces good results without exception. Although a low filtration temperature near the solidification temperature produces more desirable results in some cases, filtration is preferably performed at a temperature causing no trouble in the filtration work when solidification proceeds during filtration in some cases.

The reduced-pressure treatment is a means for removing a solvent, dissolved gas and odor which deteriorate the performance of the resin generally produced by curing the polymerizable composition. Since a dissolved solvent generally decreases the refractive index of the resultant resin and deteriorates the heat resistance thereof, the dissolved solvent may be removed as much as possible. Although the allowable amount of the dissolved solvent depends on the structure of the compound constituting the polymerizable composition to be handled and the structure of the dissolved solvent, and is not limited, the allowable amount is usually preferably not more than 1% and more preferably not more than 5,000 ppm. The dissolved gas inhibits polymerization or causes the problem of mixing bubbles in the resultant resin, and is thus preferably removed. Particularly, a moisture gas such as water vapor or the like is preferably removed by bubbling with a dry gas. The amount of the dissolved gas can be determined depending on the structure of the compound constituting the polymerizable composition, and the physical properties, structure and kind of the dissolved gas.

As a method for producing the polymerizable composition according to the present invention, a mixture of the compound represented by the above general formula (1), the compound represented by the above general formula (3) (for example, the above general formula (5)) and, if necessary, the aforementioned various other polymerizable compounds, a polymerization catalyst, an additive and the like introduced thereinto all at once may be typically melted by heating and mixed.

The resultant polymerizable composition is useful, for example, as a raw material monomer composition for use in a transparent resin having an extremely high refractive index.

Furthermore, the resultant polymerizable composition can be usually polymerized and cured in accordance with a known method for polymerizing a thietane group-containing compound.

The kind and amount of the polymerization catalyst used for obtaining a cured resin, and the kind and ratio of the monomer are determined depending on the structure of the compound constituting the polymerizable composition.

In curing and molding the polymerizable composition of the present invention, a known molding method may be used according to purposes, and various substances, such as a stabilizer, a resin modifier, a chain extender, a crosslinking agent, a light stabilizer including a typical hindered amine light stabilizer (HALS), an ultraviolet absorber including a typical benzotriazole ultraviolet absorber, an antioxidant including a typical hindered phenolic antioxidant, a coloring inhibitor, a filler, an external mold releasing agent including a typical silicone type external mold releasing agent, or an internal mold releasing agent including typically acidic phosphate, and a surface active agent such as quaternary ammonium salt, quaternary phosphonium salt internal mold releasing agent or the like, an adhesion improving agent and the like may be added. Herein, the internal mold releasing agent includes those catalysts exhibiting the mold release effect among the aforementioned various catalysts.

Although the amount of each of the aforementioned various additives which can be added is different depending on the kind, structure and effect of each additive, and is not limited, the adding amount is usually in the range of not less than 0.001 and not more than 10 weight % and preferably in the range of not less than 0.01 and not more than 5 weight %, based on the total weight of the polymerizable composition. Within these ranges, a sufficiently cured resin can be produced, and the obtained resin has good transparency and optical physical properties in some cases.

For example, when a hindered amine light stabilizer (HALS) and a phenolic antioxidant, a phosphite type antioxidant or a thioether type antioxidant are added, the color tone of the resin is improved in some cases. In particular, when a hindered amine light stabilizer (HALS) is added, the color tone of the resin is greatly improved in some cases. Examples of the hindered amine light stabilizer (HALS) include ADK STAB LA-77, LA-57, LA-52, LA-67, LA-62, LA-68, LA-63, LA-87, LA-82 and the like manufactured by ADEKA Corporation, but are not restricted thereto.

The resin is obtained by polymerization of the aforementioned polymerizable composition. Examples of the polymerization method include various known methods used when producing plastic lenses. A typical method includes a casting polymerization.

When casting polymerization of the polymerizable composition of the present invention is carried out, the polymerizable composition is degassed under reduced pressure or filtered off using a filter as required, and then the polymerizable composition is poured into a mold, and if necessary, heated for carrying out polymerization. In this case, it is preferable to carry out polymerization by slowly heating from a low temperature to a high temperature.

The aforementioned mold is composed of, for example, two pieces of mirror surface-ground molds via a gasket made of polyethylene, an ethylene vinyl acetate copolymer, polyvinyl chloride and the like. Typical examples of the mold include, though not restricted to, combined molds such as glass and glass, glass and plastic plate, glass and metal plate, and the like. The mold may comprise two pieces of molds fixed by a tape such as a polyester adhesive tape or the like. In addition, a known method such as the mold release process may be performed for the mold, as needed.

When carrying out casting polymerization, the polymerization temperature is affected by the polymerization conditions such as the kind of polymerization initiator and the like, and is not limited. But, it is usually not less than −50 and not more than 200 degrees centigrade, preferably not less than −20 and not more than 170 degrees centigrade, and more preferably not less than 0 and not more than 150 degrees centigrade.

The polymerization time is affected by the polymerization temperature, but it is usually not less than 0.01 and not more than 200 hours and preferably not less than 0.05 and not more than 100 hours. Polymerization can also be carried out in combination of several temperatures by conducting fixed temperature, temperature elevation, temperature dropping and the like as required.

Furthermore, the polymerizable composition of the present invention can also be polymerized by applying the active energy line such as an electron beam, ultraviolet light, visible light or the like. At this time, a radical polymerization catalyst or a cationic polymerization catalyst for initiating polymerization by the active energy line is used as required.

After the thus-obtained resin is cured, it may be subjected to an annealing process as required. Furthermore, for purposes of anti-reflection, high hardness grant, wear resistance improvement, anti-fogging property grant or fashionability grant, various known physical or chemical processes such as surface polishing, antistatic process, hard coat process, non-reflective coat process, dyeing process, photochromic process (for example, photochromic lens process and the like) and the like may be performed as needed.

The resin obtained by polymerization of the polymerizable composition of the present invention has high transparency, good heat resistance and mechanical strength, while attaining a high refractive index. So, the resin is useful, for example, as a resin for use in optical components such as plastic lenses and the like.

Examples of the optical component include various plastic lenses such as a spectacle lens for vision correction, a lens for cameras, a fresnel lens for liquid crystal projectors, a lenticular lens, a contact lens and the like; a sealing material for light emitting diodes (LED); an optical waveguide; an optical adhesive used for the junction of an optical lens and an optical waveguide; an anti-reflection film to be used for optical lenses; and a transparent coating or transparent substrate used for a liquid crystal display member such as a substrate, a light guiding plate, a film, a sheet and the like.

EXAMPLES

The present invention is now illustrated in detail below with reference to Examples. However, the present invention is not restricted to these Examples.

Reference Production Example 1

According to the method as described in Patent Document 2 (Japanese Patent Laid-open No. 2003-327583), 3-thiethanol was synthesized. Furthermore, the resulting 3-thiethanol was used to synthesize 3-mercaptothietane.

Namely, into a reactor equipped with a stirring device and a thermometer were added 190 g (2.50 mole) of thiourea, 253 g of a 35 weight % hydrochloric acid solution and 250 g of water, and the resulting mixture was stirred to give a reaction solution. While the reaction solution was stirred, 156 g (1.73 mole) of 3-thiethanol was added dropwise to the reaction solution over 1 hour. After completion of the dropwise addition, the resulting solution was stirred at 30 degrees centigrade for 24 hours for carrying out the reaction, and then 177 g of 24 weight % ammonia water was added dropwise thereto over 1 hour. The solution was further reacted at 30 degrees centigrade for 15 hours, and then allowed to stand for taking out an organic layer (under layer) to obtain 134 g of a crude product. The resulting crude product was distilled off under reduced pressure to collect a fraction of a boiling point of 40 degrees centigrade under 106 Pa to obtain a desired product of a colorless transparent liquid, that is, 3-mercaptothietane.

Reference Production Example 2

In this Example, tetrakis(thietanylthio)tin (IV) (a compound represented by the following formula (5)) was synthesized.

11.15 g (0.105 mole) of 3-mercaptothietane synthesized in Reference Production Example 1 was added into 50 g of pure water, and subsequently 41.2 g (0.103 mole) of an aqueous solution of 10% NaOH was added dropwise into the mixture at room temperature over 40 minutes. Next, the reaction solution was heated to 30 degrees centigrade, and 65.2 g (corresponding to 0.025 mole of tin tetrachloride) of an aqueous solution of 10% tin tetrachloride was added dropwise thereto at the same temperature over 4 hours. After completion of the dropwise addition, the resulting solution was further stirred at the same temperature for 2 hours. 100 ml of chloroform was added to this reaction mixture for separating an organic layer and an aqueous layer. The organic layer was washed twice with 100 ml of pure water and then dried using anhydrous sodium sulfate. The solvent was distilled off from this extract to obtain 13.40 g of tetrakis(thietanylthio)tin (IV),

[Chemical Formula 25]

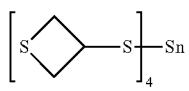
(5)

Reference Production Example 3

In this Example, mercaptopropylene sulfide (a compound represented by the following formula (20)) was synthesized.

49.0 g (0.39 mole: commercial product (a product of Tokyo Chemical Industry Co., Ltd.)) of 2,3-dimercapto-1-propanol was dissolved in 250 g of dichloromethane and was cooled to 5 degrees centigrade using an ice water bath. To this solution was added dropwise a solution obtained by dissolving 35.6 g of phosphorus tribromide (0.13 mole: commercial product (a product of Wako Pure Chemical Industries, Ltd.)) in 50 g of dichloromethane over 1 hour. Further, a solution obtained by dissolving 66.2 g of sodium hydrogen carbonate (0.79 mole: commercial product (a product of Wako Pure Chemical Industries, Ltd.)) in 500 g of water was introduced dropwise thereto over 1 hour, and the resulting mixture was stirred for 30 minutes and then allowed to stand for 12 hours. Subsequently, 200 g of 36% hydrochloric acid was added with stirring, and continuously stirred for 1.5 hours. Stirring was stopped and the mixture was allowed to stand, then separating into two phases, and the aqueous layer was removed. The organic layer was washed twice with 250 g of water, followed by liquid separation repeatedly, and then 20 g of magnesium sulfate was added into the organic layer and stirred for carrying out dehydration. Magnesium sulfate was removed by filtration, the filtrate was concentrated under reduced pressure using a rotary evaporator, and then the solvent was removed by reducing the pressure with a vacuum pump while bubbling nitrogen gas, whereby 40.3 g of a desired product of a light yellow transparent liquid, that is, mercaptopropylene sulfide was obtained.

[Chemical Formula 26]

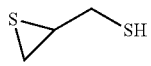
(20)

The identification data of the obtained compound is shown below.

$^{1}$H-NMR (solvent: CDCl$_3$, internal standard substance: TMS) δ: 1.70 (1H), 2.28 (1H), 2.57 (1H), 2.64 (1H), 2.93 (1H), 3.15 (1H)

$^{13}$C-NMR (solvent: CDCl$_3$) δ: 25.8, 30.7, 36.9

IR (Universal ATR method): 2544, 1438, 1421, 1345, 1245, 1201, 1155, 1094, 1041, 735, 659, 613 cm$^{-1}$ EI-MS: m/z 106(M+)

Example 1

In this Example, tris(2,3-epithiopropylthio)antimony (III) (a compound represented by the following formula (21)) was synthesized.

3.2 g (0.03 mole) of mercaptopropylene sulfide synthesized in Reference Production Example 3 was dissolved in 150 g of dehydrated tetrahydrofuran (commercial product (a product of Wako Pure Chemical Industries, Ltd.)) and was cooled to −30 degrees centigrade. To this solution was added 2.9 g of dehydrated pyridine (0.036 mole: commercial product (a product of Wako Pure Chemical Industries, Ltd.)) and stirred for 10 minutes. Further, a solution obtained by dissolving 2.3 g (0.01 mole) of antimony chloride in 40 g of dehydrated tetrahydrofuran was added dropwise thereto over 2 hours. The resulting mixture was stirred for 4 hours while maintaining at −30 degrees centigrade, and then 30 g of 1 N hydrochloric acid was added thereinto and stirred. 50 g of water was further added thereto, and then extracted with 100 g of toluene for carrying out liquid separation. The extract was washed with 50 g of water and 50 g of saturated sodium chloride solution, and then magnesium sulfate was added thereto for stirring and drying. Magnesium sulfate was removed by filtration, and the filtrate was concentrated using a rotary evaporator, followed by reducing the pressure with a vacuum pump for drying to obtain 4.3 g of a desired product of a light yellow oil containing tris(2,3-epithiopropylthio) antimony (III).

[Chemical Formula 27]

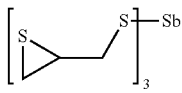
(21)

The identification data of the obtained compound is shown below.

$^{1}$H-NMR (solvent: DMSO-d6, internal standard substance: TMS) δ: 2.39 (3H), 2.61 (3H), 2.71 (3H), 2.99 (3H), 3.18 (3H)

IR (Universal ATR method): 1407, 1247, 1191, 1153, 1040, 860, 644, 610 cm$^{-1}$ Production of Polymerizable Composition and Production of Resin Cured Product by Polymerization of the Composition In the following Examples, a polymerizable composition was respectively produced using the epithio compound produced in the above Production Examples or Examples, and a resin was respectively obtained by polymerizing the polymerization composition and curing.

Physical properties of the resulting resin or optical component (lens) were evaluated in the following manner.

Appearance: Transparency was confirmed visually.

Refractive index, Abbe's number: They were measured at 20 degree centigrade using a Pulfrich refractometer.

Example 2

0.38 g of the light yellow oil produced in Example 1 was weighed in a glass beaker at room temperature (25 degrees centigrade). 1.12 g of the compound produced in Reference Production Example 1 was added thereto, and the resulting mixture was stirred for dissolving. To this solution was further added 1.5 g of the compound produced in Reference Production Example 2, and the mixture was stirred for mixing. The mixture was heated to 70 degrees centigrade, stirred for dissolving, and put into an oven kept at 80 degrees centigrade. The oven was heated for 14 hours, and then heated to 120 degrees centigrade over 4 hours, and then the polymerization was conducted at 120 for 4 hours.

A molding piece of the obtained resin was excellent in transparency and had good appearance with no distortion.

Furthermore, the refractive index and Abbe's number of the obtained resin were measured and as a result, the refractive index ne was 1.763, while the Abbe's number ve was 27.

Example 3

0.36 g of the light yellow oil produced in Example 1 was weighed in a glass beaker at room temperature (25 degrees centigrade). 0.54 g of the compound produced in Reference Production Example 1 was added thereto, and the resulting mixture was stirred for dissolving. To this solution was further added 2.1 g of the compound produced in Reference Production Example 2, and the mixture was stirred for mixing. The mixture was heated to 70 degrees centigrade, stirred for dissolving, and put into an oven kept at 80 degrees centigrade. The oven was heated for 14 hours, and then heated to 120 degrees centigrade over 4 hours, and then the polymerization was conducted at 120 for 4 hours.

A molding piece of the obtained resin was excellent in transparency and had good appearance with no distortion.

Furthermore, the refractive index and Abbe's number of the obtained resin were measured and as a result, the refractive index ne was 1.779, while the Abbe's number ve was 26.

Incidentally, in this Example, as the compound represented by the general formula (1), a compound in which $M_1$ is Sb was used. However, it was found that, even when $M_1$ was Bi, the same effect as the case of Sb was obtained.

Comparative Example 1

The compound produced in Reference Production Example 3 was used instead of the compound produced in Example 1 used in Example 3, specifically, in the following manner.

0.36 g of the light yellow oil produced in Reference Production Example 3 was weighed in a glass beaker at room temperature (25 degrees centigrade). 0.54 g of the compound produced in Reference Production Example 1 was added thereto, and the resulting mixture was stirred for dissolving. To this solution was further added 2.1 g of the compound produced in Reference Production Example 2, and the mixture was stirred for mixing. The mixture was heated to 50 degrees centigrade, stirred for dissolving, and put into an oven kept at 80 degrees centigrade. The oven was heated for 14 hours, and then heated to 120 degrees centigrade over 6 hours, and then the polymerization was conducted at 120 degrees centigrade for 2 hours.

A molding piece of the obtained resin was excellent in transparency and had good appearance with no distortion.

Furthermore, the refractive index and Abbe's number of the obtained resin were measured and as a result, the refractive index ne was 1.767, while the Abbe's number ve was 28.

In Comparative Example 1, it was found that the refractive index was lower than that of Example 3, because the antimony compound produced in Example 1 was not contained.

The invention claimed is:

1. A compound represented by the following general formula (2),

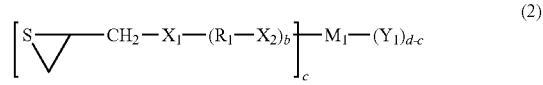

wherein, in the general formula (2), $M_1$ represents Sb or Bi; $X_1$ and $X_2$ each independently represent a sulfur atom or an oxygen atom; $R_1$ represents a divalent organic group; $Y_1$ represents a monovalent inorganic or organic group; b represents a number of 0 or an integer of not less than 1; c represents an integer of not less than 1 and not more than d; d represents a valence of $M_1$; and when d-c is not less than 2, a plurality of $Y_1$s each independently represent a monovalent inorganic or organic group and may be bonded to each other to form an $M_1$-containing ring.

2. The compound as set forth in claim 1 wherein $M_1$ is Sb.

3. The compound as set forth in claim 1, wherein b is 0.

4. The compound as set forth in claim 3, wherein $X_1$ is a sulfur atom.

5. The compound as set forth in claim 4, wherein c and d are each 3.

6. A polymerizable composition comprising the compound as set forth in claim 1.

7. The polymerizable composition as set forth in claim 6, comprising the compound represented by general formula (2), and at least one compound which is different from the compound represented by general formula (2) and selected from the group consisting of a thiol compound, an isocyanate compound, an episulfide compound, an epoxy compound, a non-metal thietane compound, a metal thietane compound, a (meth)acrylate ester compound, a vinyl compound and an oxetane compound.

8. The polymerizable composition as set forth in claim 7, comprising a metal thietane compound represented by the following general formula (3),

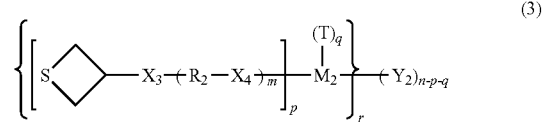

wherein, in the general formula (3), $M_2$ represents a metal atom; $X_3$ and $X_4$ each independently represent a sulfur atom or an oxygen atom; $R_2$ represents a divalent organic group; m represents a number of 0 or an integer of not less than 1; n represents a valence of $M_2$; p represents an integer of not less than 1 and not more than n; q represents a number of 0 or an integer of not less than 1 and not more than n-2; $Y_2$ represents a monovalent or divalent group; T represents an inorganic or organic group; r represents a number of 1 or 2;

when r is 1, $Y_2$ represents a monovalent inorganic or organic group, provided that r is 1 and n-p-q is not less than 2, a plurality of $Y_2$s each independently represent a monovalent inorganic or organic group, and provided that r is 1 and n-p-q is not less than 2, a plurality of $Y_2$s may be bonded to each other to form a ring containing a metal atom $M_2$;

when r is 2, and n-p-q is 1 or 2, $Y_2$ represents a divalent group, provided that r is 2 and n-p-q is 2, two $Y_2$s may form a ring along with two metal atoms $M_2$s, and provided that r is 2 and q is 2, a plurality of Ts each independently represent an inorganic or organic group.

9. The polymerizable composition as set forth in claim 8, comprising a compound in which $M_2$ in said general formula (3) is Sb or Sn.

10. The polymerizable composition as set forth in claim 8, comprising a compound in which $X_3$ in said general formula (3) is a sulfur atom.

11. The polymerizable composition as set forth in claim 8, comprising a compound represented by the following formula (4) as the compound represented by said general formula (3),

(4)

12. The polymerizable composition as set forth in claim 8, comprising a compound represented by the following formula (5) as the compound represented by said general formula (3),

(5)

13. The polymerizable composition as set forth in claim 6, further comprising a bluing agent.

14. A method for producing a resin, comprising a step of subjecting the polymerizable composition as set forth in claim 6 to casting polymerization.

15. A resin obtained by polymerizing the polymerizable composition as set forth in claim 6.

16. An optical component comprising the resin as set forth in claim 15.

* * * * *